(12) United States Patent
Klinman et al.

(10) Patent No.: US 8,222,225 B2
(45) Date of Patent: Jul. 17, 2012

(54) METHOD OF TREATING PNEUMOCONIOSIS WITH OLIGODEOXYNUCLEOTIDES

(75) Inventors: Dennis M. Klinman, Potomac, MD (US); Takashi Sato, Yokohama (JP)

(73) Assignee: The United States of America as represented by the Secretary of the Department of Health and Human Services, Bethesda, MD (US)

( * ) Notice: Subject to any disclaimer, the term of this patent is extended or adjusted under 35 U.S.C. 154(b) by 0 days.

(21) Appl. No.: 12/993,809

(22) PCT Filed: May 20, 2009

(86) PCT No.: PCT/US2009/044739
§ 371 (c)(1),
(2), (4) Date: Nov. 19, 2010

(87) PCT Pub. No.: WO2009/143292
PCT Pub. Date: Nov. 26, 2009

(65) Prior Publication Data
US 2011/0077289 A1 Mar. 31, 2011

Related U.S. Application Data

(60) Provisional application No. 61/055,102, filed on May 21, 2008.

(51) Int. Cl.
*A61K 48/00* (2006.01)
*C12N 5/00* (2006.01)
*C12N 15/00* (2006.01)
*A01N 63/00* (2006.01)

(52) U.S. Cl. .................. 514/44 R; 424/93.1; 435/320.1; 435/325; 435/455

(58) Field of Classification Search ................ 514/44 R; 424/93.1
See application file for complete search history.

(56) References Cited

U.S. PATENT DOCUMENTS

| | | | |
|---|---|---|---|
| 4,469,863 A | 9/1984 | Ts'o et al. |
| 5,023,243 A | 6/1991 | Tullis |
| 5,643,890 A | 7/1997 | Iversen et al. |
| 5,663,153 A | 9/1997 | Hutcherson et al. |
| 5,837,729 A | 11/1998 | Bourinbaiar |
| 6,214,806 B1 | 4/2001 | Krieg et al. |
| 6,288,042 B1 | 9/2001 | Rando et al. |
| 6,653,292 B1 | 11/2003 | Krieg et al. |
| 7,087,586 B2 | 8/2006 | Filion et al. |
| 7,094,766 B1 | 8/2006 | Gilchrest et al. |
| 7,119,078 B2 | 10/2006 | Jing et al. |
| 7,226,906 B2 | 6/2007 | Hunt et al. |
| 7,358,068 B2 | 4/2008 | Vaillant et al. |
| 7,514,414 B2 | 4/2009 | Klinman et al. |
| 7,514,415 B2 | 4/2009 | Klinman et al. |
| 7,951,786 B2 | 5/2011 | Klinman et al. |
| 8,053,422 B2 | 11/2011 | Klinman et al. |
| 2003/0087848 A1 | 5/2003 | Bratzler et al. |
| 2004/0132682 A1 | 7/2004 | Klinman et al. |
| 2004/0248834 A1 | 12/2004 | Klinman et al. |
| 2005/0239733 A1 | 10/2005 | Jurk et al. |
| 2006/0074039 A1 | 4/2006 | Klinman et al. |
| 2009/0082288 A1 | 3/2009 | Klinman et al. |
| 2009/0142310 A1 | 6/2009 | Klinman et al. |
| 2010/0144839 A1 | 6/2010 | Klinman et al. |

FOREIGN PATENT DOCUMENTS

| | | |
|---|---|---|
| EP | 0 092 574 | 4/1992 |
| WO | WO 83/01451 | 4/1983 |
| WO | WO 95/26204 | 9/1995 |
| WO | WO 96/02555 | 2/1996 |
| WO | WO 98/11211 | 3/1998 |
| WO | WO 98/18810 | 5/1998 |
| WO | WO 98/37919 | 9/1998 |
| WO | WO 98/40100 | 9/1998 |
| WO | WO 98/52581 | 11/1998 |
| WO | WO 99/51259 | 10/1999 |
| WO | WO 03/027313 | 4/2003 |
| WO | WO 2004/012669 | 2/2004 |
| WO | WO 2006/135434 | 12/2006 |

OTHER PUBLICATIONS

Dai et al., "Aberrant Expression of Nucleostemin Activates p53 and Induces Cell Cycle Arrest via Inhibition of MDM2," *Molecular and Cellular Biology* 28(13): 4365-4376 (Jul. 2008).
Fei et al., "Egr-1 Mediates $SiO_2$-driven Transcription of Membrane Type Matrix Metalloproteinase in Macrophages," *Journal of Huazhong University of Science and Technology* 27(1):13-16 (2007).
Fubini and Hubbard, "Reactive Oxygen Species (ROS) and Reactive Nitrogen Species (RNS) Generation by Silica in Inflammation and Fibrosis," *Free Rad. Biol. Med.* 34:1507-1516 (2003).
Fujimura, "Pathology and Pathophysiology of Pneumoconiosis," *Curr. Opin. Pulm. Med.* 6:140-144, (2000).
Huaux, "New Developments in the Understanding of Immunology in Silicosis," *Curr. Opin. Allerg. Clin. Immun.* 7:168-173 (2007). International Search Report and the Written Opinion from the prior PCT Application No. PCT/US2009/044739, 7 pages (mailed Dec. 30, 2009).
Klinman et al., "Synthetic Oligonucleotides as Modulators of Inflammation," *J. Leukoc. Biol.* 180:7648-7654 (Sep. 2008).
Klinman et al., "Therapeutic Potential of Oligonucleotides Expressing Immunosuppressive TTAGGG Motifs," Ann. N.Y. Acad. Sci., 1058:87-95 (2005).
Migliaccio et al., "The IL-4Rα pathway in Macrophages and its Potential Role in Silica-induced Pulmonary Fibrosis," *Journal of Leukocyte Biology* 83:630-639 (Mar. 2008).
Peter et al., "Characterization of Suppressive Oligodeoxynucleotides that Inhibit Toll-like Receptor-9-mediated Activation of Innate Immunity," *Immunology* 123:118-128 (2007).

(Continued)

*Primary Examiner* — Sumesh Kaushal
(74) *Attorney, Agent, or Firm* — Klarquist Sparkman, LLP

(57) ABSTRACT

Methods are disclosed for treating, preventing or reducing the risk of developing occupational lung diseases, such as pneumoconiosis. In several embodiments, the methods include administering a therapeutically effective amount of the suppressive ODN to a subject having or at risk of developing a pneumoconiosis, thereby treating or inhibiting the pneumoconiosis. In several examples, thee subject can have or be at risk of developing silicosis, asbestosis or berryliosis. The method can include selecting a subject exposed to, or at risk of exposure to, inorganic particles, including, but not limited to silica, asbestos, berrylium, coal dust, or bauxite.

16 Claims, 10 Drawing Sheets

OTHER PUBLICATIONS

Pisetsky and Reich, "Inhibition of Murine Macrophage IL-12 Production by Natural and Synthetic DNA," *Clinical Immunology* 96, 3:198-204 (Sep. 2000).

Sato et al., "Suppressive Oligodeoxynucleotides Inhibit Silica-Induced Pulmonary Inflammation," *Journal of Immunology* 180:7648-7654 (2008).

Sawyer et al., Beryllium-stimulated Reactive Oxygen Species and Macrophage Apoptosis, Free Rad. Biol. Med., 38:928-937, 2005.

Shirota et al., "Suppressive Oligodeoxynucleotides Inhibit Th1 Differentiation by Blocking IFN-γ- and IL-12-Mediated Signaling," *Journal of Immunology* 173:5002-5007 (2004).

Shirota et al., "Suppressive Oligodeoxynucleotides Protect Mice from Lethal Endotoxic Shock," *Journal of Immunology* 174:4579-4583 (2005).

Shukla et al., "Multiple Roles of Oxidant in the Pathogenesis of Asbestos-Induces Diseases," *Free Rad. Biol. Med.* 34:1117-29 (2003).

Tinkle et al., "Cytokine Production by Bronchoalveolar Lavage Cells in Chronic Beryllium Disease," *Environmental Health Perspectives* 104(Supplement 5):969-971 (Oct. 1996).

Yamada et al., "Suppressive Oligodeoxynucleotides Inhibit CpG-induced Inflammation of the Mouse Lung," *Crit. Care Med.* 32(10):2045-2049 (2004).

Zhu et al., "Inhibition of Murine Dendritic Cell Activation by Synthetic Phosphorothioate Oligodeoxynucleotides," *Journal of Leukocyte Biology* 72:1154-1163 (Dec. 2002).

Zhu et al., "Inhibition of Murine Macrophage Nitric Oxide Production by Synthetic Oligonucleotides," *Journal of Leukocyte Biology* 71:86-694 (Apr. 2002).

Balagurumoorthy et al., "Hairpin and parallel quartet structures for telomeric sequences," *Nucleic Acid Res.* 20(15):4061-4067 (Aug. 1992).

Battegay, "Angiogenesis: mechanistic insights, neovascular diseases, and therapeutic prospects," *J. Molec. Med.* 73(7): 333-346 (1995).

Beck and D'Amore, "Vascular development: cellular and molecular regulation," *FASEB J.* 11(5):365-373 (1997).

Bjersing et al., "Anti-proliferative effects of phosphodiester oligodeoxynucleotides," *Immunobiology* 209(8):637-45 (2004).

Chatziantoniou, "Telomerase: Biological Function and Potential Role in Cancer Management," *Pathology Oncology Research* 7(3): 161-170 (2001).

Chen et al., "Identification of methylated CpG motifs as inhibitors of the immune stimulatory CpG motifs," *Gene Ther.* 8(13):1024-1032 (2001).

Dong et al., "Suppressive Oligodeoxynucleotides Delay the Onset of Glomerulonephritis and Prolong Survival in Lupus-Prone NZB X NZW Mice," *Arthritis & Rheumatism* 52(2):651-658 (Feb. 2005).

Dong et al., "Suppressive Oligonucleotides Protect Against Collagen-Induced Arthritis in Mice," *Arthritis & Rheumatism* 50(5):1686-1689 (May 2004).

Enokizono et al., "Structure of hnRNP D Complexed with Single-stranded Telomere DNA and Unfolding of the Quadruplex by Heterogeneous Nuclear Ribonucleoprotein D," *J. Biological Chemistry* 280(19):18862-18870 (2005).

Gaudric et al., "Quantification of Angiogenesis due to Basic Fibroblast Growth Factor in a Modified Rabbit Corneal Model," *Ophthal. Res.* 24: 181 (1992).

Gursel, I., et al., "Repetitive Elements in Mammalian Telomeres Suppress Bacterial DNA-Induced Immune Activation," J. Immunology 171:1393-1400 (2003).

Gursel, I., et al., "Sterically Stabilized Cationic Liposomes Improve the Uptake and Immunostimulatory Activity of CpG Oligonucleotides," *J. Immunol.* 167: 3324 (2001).

Gursel, M., et al., "Differential and competitive activation of human immune cells by distinct classes of CpG oligodeoxynucleotide," *J. Leuko. Biol.* 71:813-820 (2002).

Han & Hurley, "G-quadruplex DNA: a potential target for anti-cancer drug design," *Trends Pharmacol. Sci.* 21:136-142 (2000).

Hartmann et al., "CpG DNA: A potent signal for growth, activatio, and maturation of human dendritic cells," *Proc. Natl. Acad. Sci. USA* 96:9305-9310 (1999).

Ho et al., "An Immunomodulatory GpG Oligonucleotide for the Treatment of Autoimmunity via the Innate and Adaptive Immune Systems," *J. Immunol.* 171:4920-4926 (2003).

Jing, "Developing G-quartlet oligonucleotides as novel anti-HIV agents: focus on anti-HIV drug design," *Investig. Drugs* 9(8):1777-1785 (Aug. 2000).

Klinman et al., "Activiation of the innate immune system by CPG oligodeoxynucletides: immuniprotective activity and safety," *Springer Semin. Immunopathol.* 22:173-83 (2000).

Klinman et al., "Synthetic oligonucleotides as modulations of inflammation," *J. Leuk. Biol.* 84:958-964 (Oct. 2008).

Klinman et al., "CpG motifs present in bacterial DNA rapidly induce lymphocytes to secrete interleukin 6, interleukin 12, and interferon γ," *Proc. Natl. Acad. Sci. USA* 93: 2879 (1996).

Klinman et al., "Contribution of CpG motifs to the immunogenicity of DNA vaccines," *J. Immunol.* (Abstract) 158:3635-3639 (1997).

Krieg et al., "Sequence motifs in adenoviral DNA block immune activation by stimulatory CpG motifs," *Proc. Natl. Acad Sci. USA* 95:12631-12636 (1998).

Krieg et al., "CpG motifs in bacterial DNA trigger direct B-cell activation," *Nature* 374: 546 (1995).

Krieg, "From A to Z on CpG," *Trends Immunol.* 23(2):64-65 (2002).

Lenert et al., "CpG Stimulation of Primary Mouse B Cells is Blocked by Inhibitory Oligodeoxyribonucleotides at a Site Proximal to NF-κB Activation," *Antisense Nucleic Acid Drug Dev.* 11, 247-256 (2001).

Liang et al., "Activation of Human B Cells by Phosphorothioate Oligodeoxynuceliotides,"*J. Clin. Invest.* 98:1119 (1996).

Lichtenberg et al., "The Rat Subcutaneous Air Sac Model: A Quantitative Assay of Antiangiogenesis in Induced Vessels," *Pharmacol Toxicol.* 84: 34 (1999).

Murchie & Lilley, "Tetraplex folding of telemere sequences and the inclusion of adenine bases," *EMBO J.* 13:993-1001 (1994).

Pisetsky et al., "Immunological Properties of Bacterial DNA," *NY Acad. Sci.* 772:152 (1995).

Pisetsky et al., "Inhibition of Murine Macrophage IL—12 Production by Natural and Synthetic DNA," *Clin. Immunol.* 96, 198-204 (2000).

Quarcoo et al., "Inhibition of signal transducer and activator of transcription 1 attenuates allergen-induced airway inflammation and hyperreactivity," *J. Allergy Clin. Immunol.* 114(2):288-95 (2004).

Roman, et al., "Immunostimulatory DNA sequences function as T helper-1-promting adjuvants," *Nature Medicine* 3:849 (1997).

Schwartz et al., "Bacterial DNA or Oligonucleotides Containing Unmethylated CpG Motifs Can Minimize Lipopolysaccharide-Induced Inflammation in the Lower Respiratory Tract Through an IL-12-Dependent Pathway," *J. Immunol.* 163:224-231 (1999).

Schwartz et al., CpG Motifs in Bacterial DNA Cause Inflammation in the Lower Respiratory Tract, *J. Clin. Invest.* 100:68-73 (1997).

Shirota et al., "Suppressive Oligodeoxynucleotides Protect Mice from Lethal Endotoxic Shock," J. Immunology 174:4579-4583 (2005).

Stunz et al., "Inhibitory oligonecletides specifically block effects of stimulatory CpG oligonucleotides in B cells," *Eur. J. Immunol.* 32:1212-1222 (2002).

Verthelyi et al., "Human Peripheral Blood Cells Differentially Recognize and Respond to Two Distinct CpG Motifs," *J. Immunol.* 166:2372-2377 (2001).

Vialas et al., "Oxidative Damage Generated by an Oxo-Metalloporphyrin into the Human Telemeric Sequence," *Biochemistry* 39:9514-9522 (2000).

Williamson, "G-quartlets in biology: Reprise," *PNAS* 90:3124 (1993).

Yamada et al., "Effect of Suppressive DNA on CpG-Induced Immune Activation," *J. Immunol.* 169:5590-5594 (2002).

Yamamoto et al., "Unique Palindromic Sequences in Synthetic Oligonucleotides are Required to Induce INF and Augment INF-Mediated Natural Killer Activity," *J. Immunol.* 148:4072 (1992).

Yi et al., "Rapid Immune Activation by CPG Motifs in Bacterial DNA," *J. Immun*. 157: 5394 (1996).

Zeuner et al., "Reduction of CpG-Inuced Arthritis by Suppressive Oligodeoxynucleotides," *Arthritis & Rheumatism*, 46(8):2219-2224 (2002).

Zhao et al., "Requirements for effective inhibition of immunostimulatory CpG motifs by neutralizing motifs," *Antisense Nucleic Acid Drug Dev*. 10(5):381-389 (2000).

Zheng et al., "DNA containing CPG motifs induces angiogenesis," *PNAS* 99(13):8944-8949 (2002).

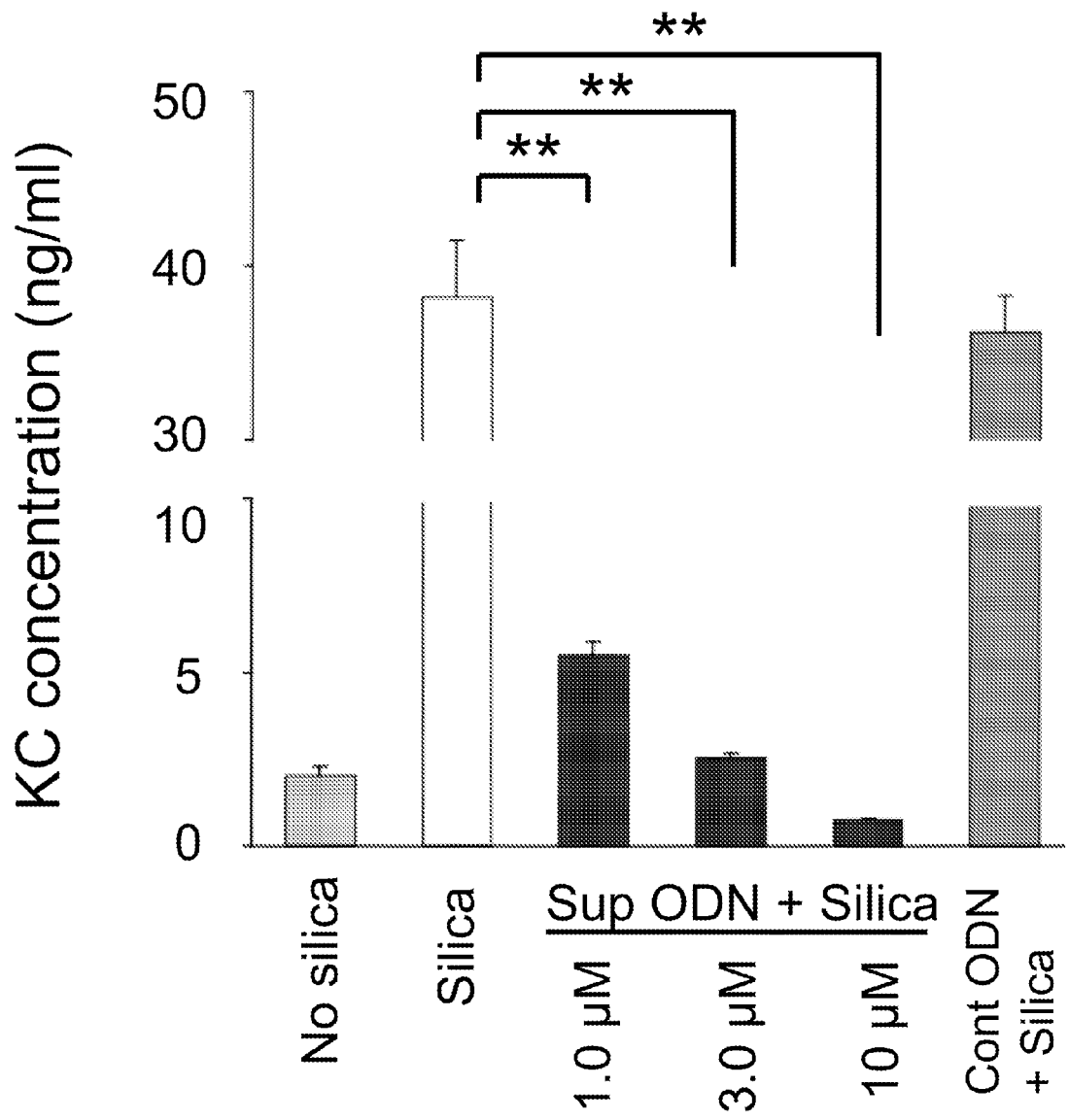

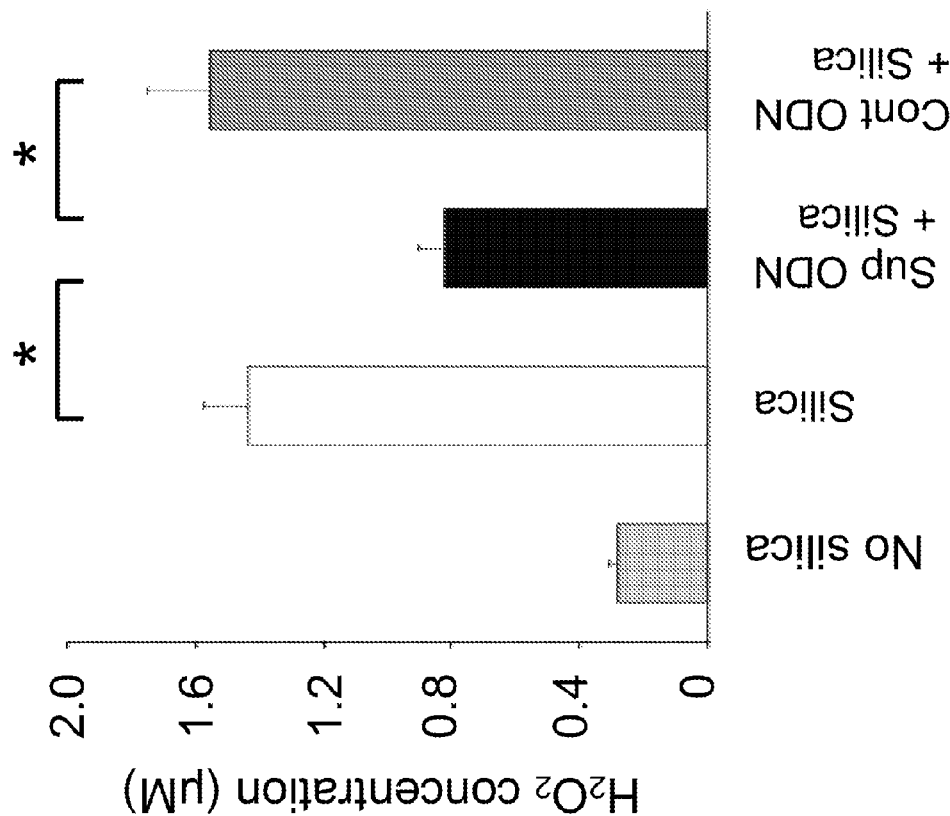
FIG. 2A RAW264.7
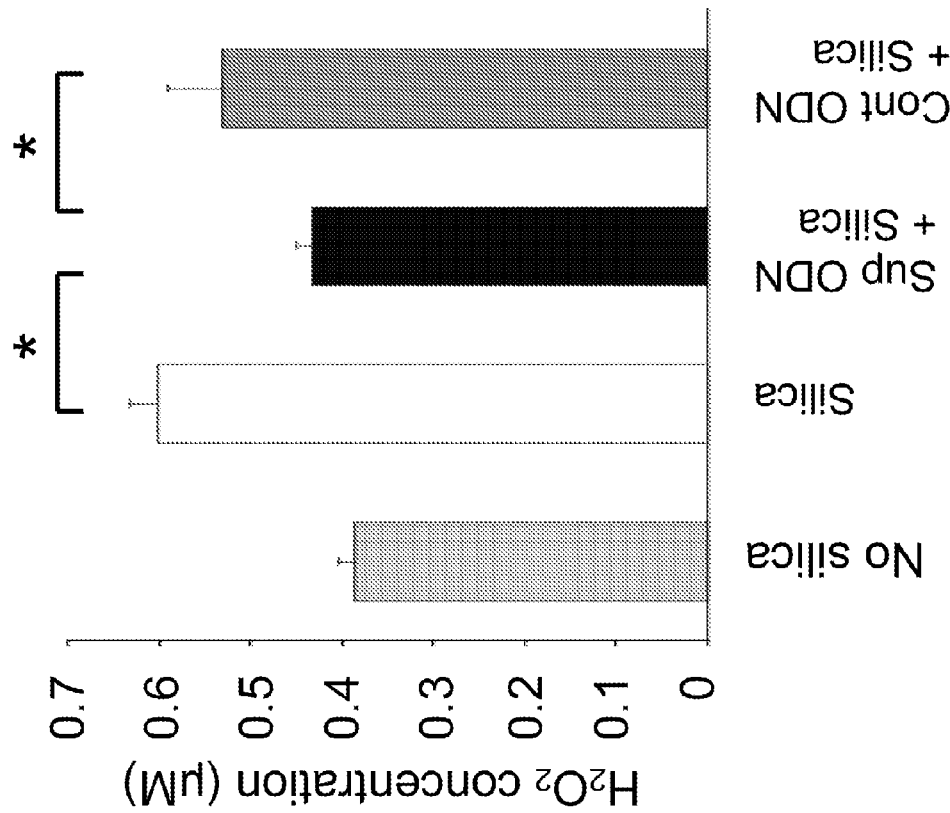
FIG. 2B Peritoneal macrophages

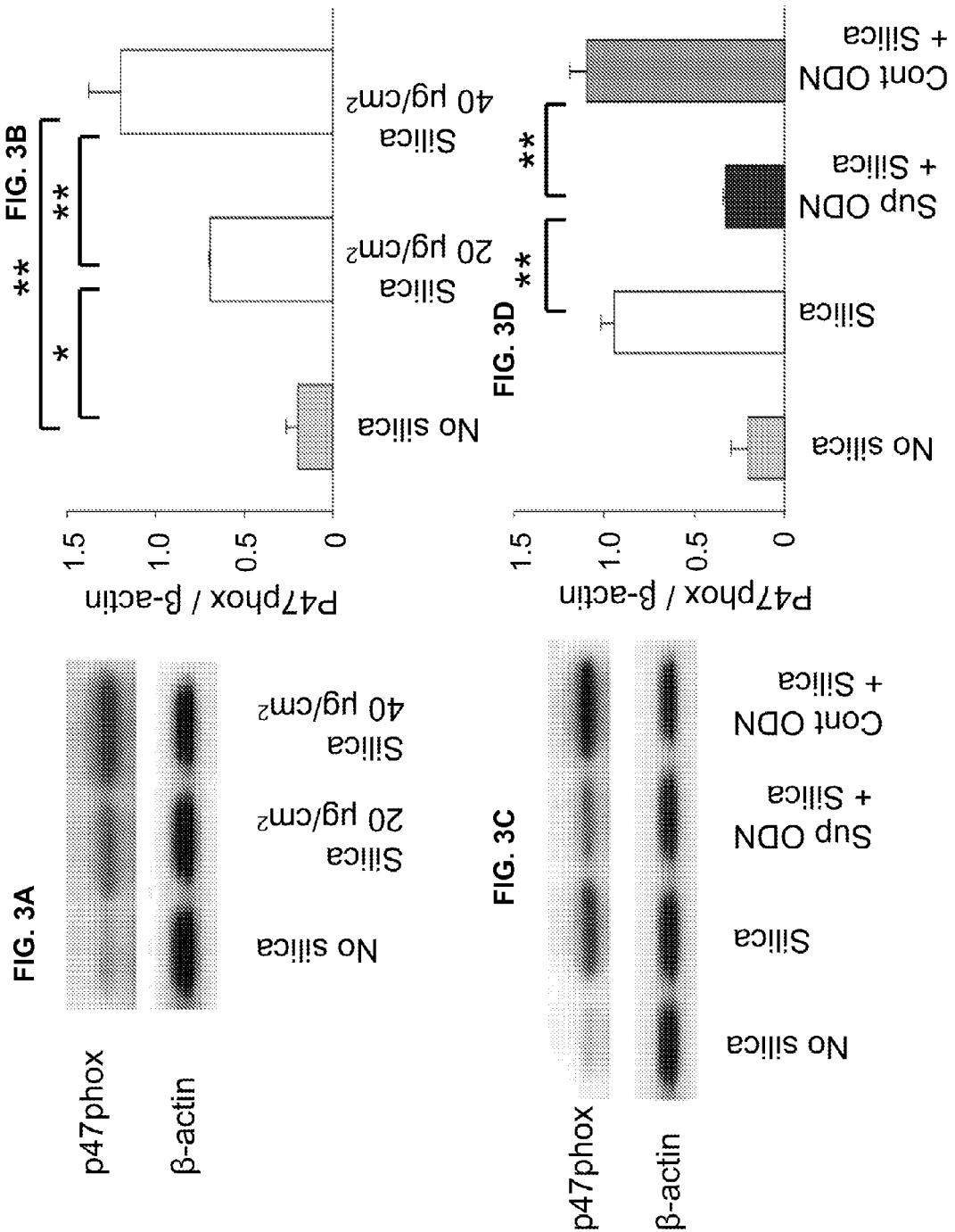

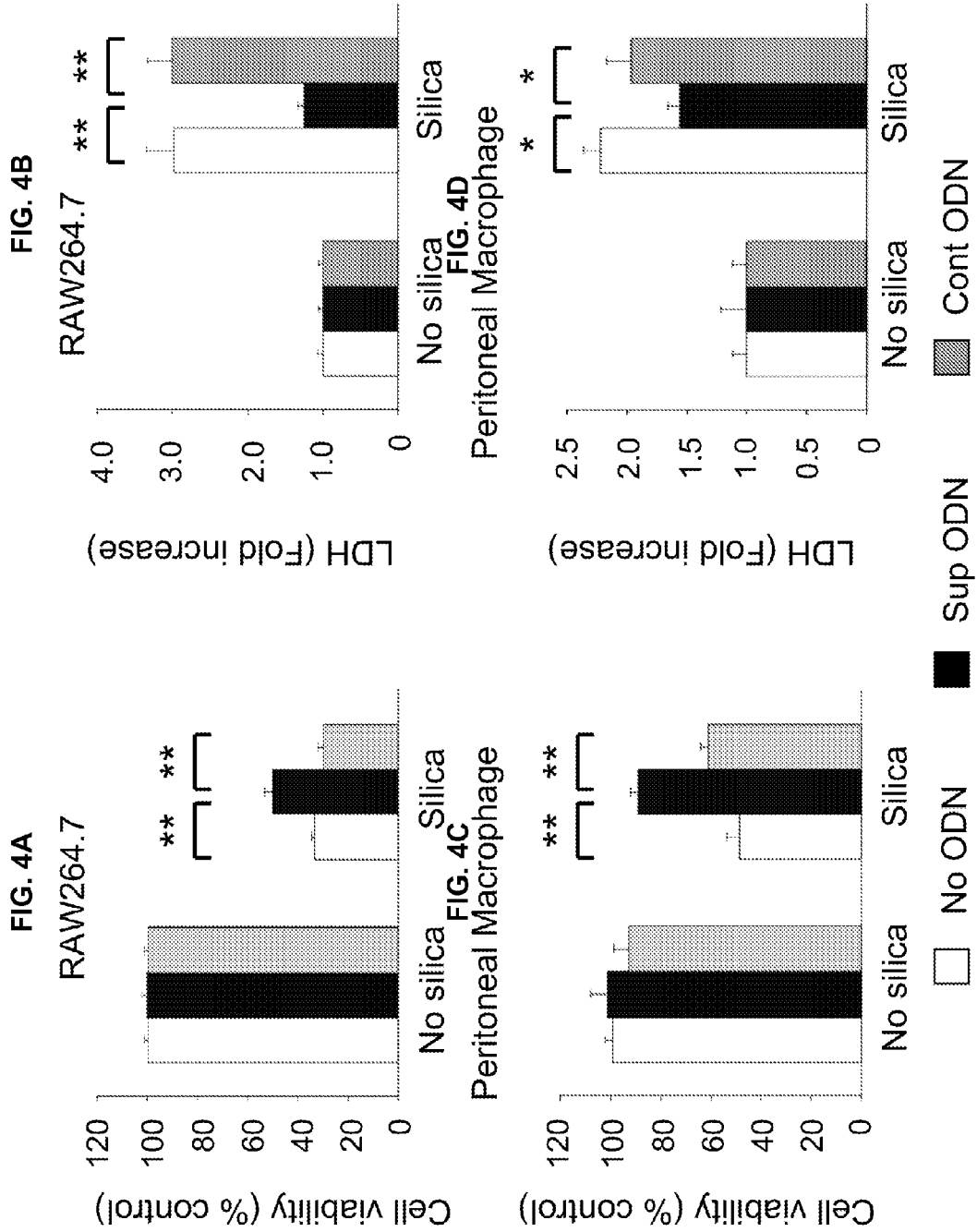

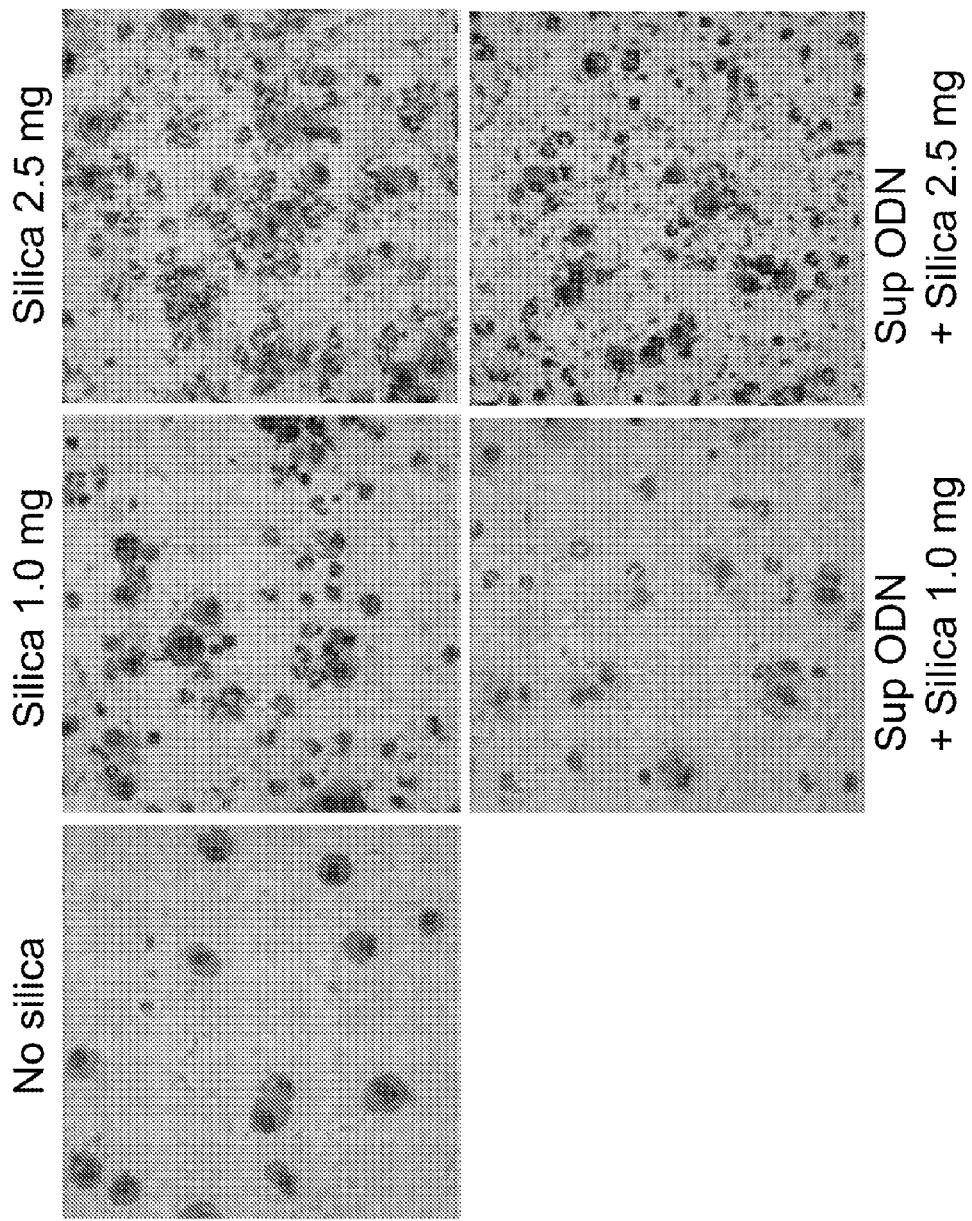

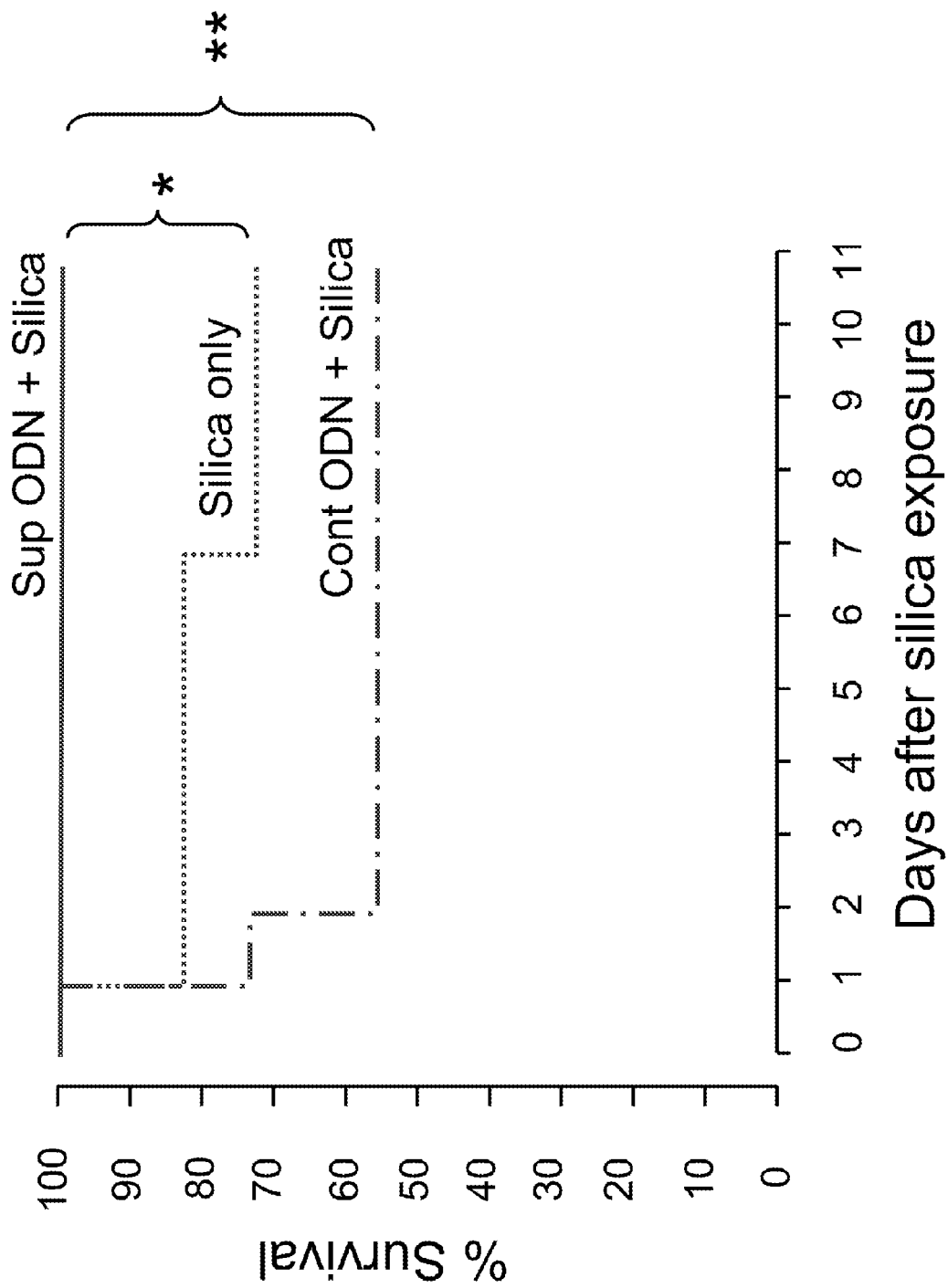

METHOD OF TREATING PNEUMOCONIOSIS WITH OLIGODEOXYNUCLEOTIDES

CROSS REFERENCE TO RELATED APPLICATIONS

This is the U.S. national stage of PCT Application No. PCT/US2009/044739, filed May 20, 2009, which was published in English under PCT Article 21(2), which in turn claims the benefit of U.S. Provisional Application No. 61/055,102, filed May 21, 2008, which is incorporated by reference herein in its entirety.

FIELD

The present disclosure relates to the field of pneumoconiosis, specifically to the reduction of the immune response to inorganic particles such as silica and/or asbestos.

BACKGROUND

Inhalation of inorganic (e.g., mineral) dust is known to induce pathological changes in lung tissue leading to pneumoconiosis. Inorganic dust may include, but is not limited to silica, asbestos, cristobalite, man-made vitreous fibers, and the like. Pneumoconioses include silicosis, asbestosis, and Word Trade Center cough.

The inhalation of dust containing crystalline silica particles causes silicosis, an incurable lung disease which progresses even after dust exposure ceases. The World Heath Organization (WHO) estimates that over a million workers in the United States are exposed to silica dust annually, and that thousands worldwide die each year from silicosis (Verma et al., *Occup. Environ. Med.* 59:205-213, 2002). The pulmonary inflammation caused by silica inhalation is characterized by a cellular infiltrate and the accumulation of chemokines, cytokines (including TNF-, IL-1, and IL-6) and reactive oxygen species (ROS) in bronchoalveolar lavage (BAL) fluid (see, for example, Davis et al., *Am. J. Respir. Cell Mol. Biol.* 22:491-501, 2000; Huax et al., *J. Immunol.* 169:2653-2661, 2002).

Macrophages are the predominant immune cell type present in alveolar spaces where they play an important role in the lung pathology associated with silica inhalation (Davis et al. supra, 2002). The uptake of silica particles by macrophages triggers the production of reactive oxygen species (ROS) including $H_2O_2$ via the oxidative stress pathway, which in turn contributes to pulmonary damage and macrophage death (see, for example, Rimal et al., *Curr. Opin. Pulm. Med.* 11:169-173, 2005; Sayes, *Toxicol. Sci.* 97:163-180, 2007; Persson, *Toxicol. Lett.* 159:124-133, 2005; Giorgio, *Nat. Rev. Mol. Cell Biol.* 8:722-728, 2007). The dominant pathway by which silica-stimulated macrophages produce $H_2O_2$ involves the activation of NADPH oxidase (Fubini and Bubbard, *Free Radic. Biol. Med.* 34:1507-1516, 2007; Persson, supra, 2007; Giorgio et al, supra, 2007; Bedard and Krause, *Physiol Rev.* 87:245-313, 2007). In this pathway, cytoplasmic p47phox interacts with p67phox to form an active gp91 enzyme complex, with changes in ROS production correlating closely with levels of p47phox expression (see, for example, Teissier et al., *Circ. Res.* 95:1174-1182, 2005; Von and Brune, *J. Immunol.* 169:2619-2626, 2002).

There is a well established murine model of acute silicosis (Huax et al., *J. Immunol.* 169:2653-2661, 2002; Callis et al., *J. Lab Clin. Med.* 105:547-553, 1985; Hubbard, *Lab Invest* 61:46-52, 1989). While human disease typically progresses over many years (even decades), pulmonary inflammation in this model system develops rapidly and resolves over the course of several weeks. Nevertheless, this murine model shares important characteristics with human silicosis, including acute neutrophilic extravasation, increased protein in BAL, and progressive fibrosis (Callis et al., supra, 1985; Suzuki et al., *Thorax* 51:1036-1042, 1996; Faffe et al., *J. Appl. Physiol* 90:1400-1406, 2001). This murine model can be used to identify new agents for the treatment of silicosis.

Various forms of asbestos, such as chrysotile, crocidolite and amosite, have also been found to be toxic to mammals, particularly when inhaled. Inhalation of asbestos can induce one or more of inflammation and pulmonary fibrosis, either or both of which can lead to pulmonary disease such as respiratory impairment, as well as promote development of malignant pleural mesotheliomas. It is believed that inhalation of asbestos can induce pulmonary disease utilizing similar mechanisms as the inhalation of silica. For example, inhaled asbestos (for example, crystalline particles and/or fibers) typically contacts pulmonary macrophages which induces an inflammatory response characterized by production and release of toxic, reactive oxygen intermediates in the lung. Additionally, in vivo and in vitro studies show that alveolar macrophages, following exposure to asbestos, can release neutrophil chemotaxins such as interleukin (IL)-8 which can further contribute to inflammation in the respiratory tract.

Additional concerns for inhalation exposure to harmful inorganic dust have been raised by the collapse of the World Trade Center and the smoke from the associated fires. The steel columns of the World Trade Center were coated with sprayed asbestos as a fire retardant. Upon the collapse of the buildings, a fine white dust could be seen, the dust including pulverized concrete, tons of fine particles of asbestos and other inorganic dust such as particles containing one or more of silicon, sulfur, titanium, vanadium, and nickel. Some reports estimate that, as a result of the collapse, nearly 5,000 tons of asbestos were released in Manhattan. Those people in the vicinity of the collapsed buildings have been and may continue to be exposed to such inorganic dusts. Symptoms of exposure include chest tightness, bloody noses, sinus infections, and other respiratory ailments, including what is now termed as the "World Trade Center cough" (a persistent cough resulting from pulmonary inflammation). Nearly one in four firefighters who have been working at the Ground Zero site complain of having the World Trade Center cough. Of these firefighters, at least 10% have positive CAT scans showing pulmonary inflammation as a result of their exposure.

Bronchiolitis obliterans also can be initiated by inhalation of particles (inorganic dust, organic dust, and a combination thereof) in the small conducting airways of the respiratory tract, and which leads to inflammation of these airways that can ultimately result in irreversible airway obstruction. Examples of occupations that can develop such bronchiolitis through the inhalation of particles includes silo workers, textile workers, and workers in the food industry.

Hence, there is a need for a method for inhibiting pathogenesis induced by inhalation of particles (inorganic dust, organic dust, or a combination thereof). Specifically, there is a need for a method of therapy to treat or prevent pulmonary disease (including respiratory ailments) in an individual, wherein administered to the individual is a composition in an amount effective to reduce inflammation induced by inhalation of inorganic dust such as silica or asbestos.

SUMMARY

Methods are disclosed herein for treating, including preventing or reducing the risk of develping occupational lung diseases, such as pneumoconiosis. Methods are also disclosed herein for decreasing the production of reactive oxygen species in the lung, for increasing the survival of macrophages, and for decreasing the toxicity of reactive oxygen species for macrophages in the lung. In several embodiments, the methods include administering a therapeutically effective amount of the suppressive oligodeoxy nucleotide (ODN) to a subject having or at risk of developing a pneumoconiosis, thereby treating or inhibiting the pneumoconiosis.

In one example, the subject has or is at risk of developing silicosis. In another example, the subject has or is at risk of developing asbestosis. In a further example, the subject has or is at risk of developing berryliosis. The method can include selecting a subject exposed to, or at risk of exposure to, inorganic particles, including, but not limited to silica, asbestos, berrylium, coal dust, or bauxite.

The foregoing and other features and advantages will become more apparent from the following detailed description of several embodiments, which proceeds with reference to the accompanying figures.

BRIEF DESCRIPTION OF THE FIGURES

FIG. 1 is a bar graph showing the effect of suppressive oligodeoxynucleotides (ODN) on silica-induced chemokine production by MM14.Lu cells. MM14.Lu cells were cultured with 40 g/cm2 silica for 24 hours with or without 3 μM ODN (unless otherwise noted). Supernatants were collected and assayed for KC concentration. Results represent the mean±SE of three independent experiments. **, $p<0.01$.

FIGS. 2A and 2B are bar graphs showing the effect of suppressive ODN on silica-induced $H_2O_2$ production. RAW264.7 cells (FIG. 2A) or freshly isolated peritoneal macrophages (FIG. 2B) were cultured with 40 g/cm2 silica for 24 hours with or without 3 μM ODN. Cell viability and $H_2O_2$ levels were measured using an $Fe^{3+}$-xylenol orange based assay. To facilitate comparisons between experiments, $H_2O_2$ concentration was standardized as a function of viable cell number/culture. To insure that $H_2O_2$ concentration was monitored, background activity in catalase-treated cultures was subtracted. Results represent the mean±SE $H_2O_2$ concentration from three independent experiments. *, $p<0.05$.

FIGS. 3A-3D are bar graphs and digital images showing the effect of suppressive ODN on silica-dependent p47phox induction. RAW264.7 cells were incubated with 20-40 μg/cm$^2$ of silica±3 μM ODN for 24 hr. While RAW264.7 cells stimulated with 20-40 μg/cm$^2$ silica showed dose-dependent increase in p47phox induction (FIGS. 3A and 3B), 3 μM of suppressive ODN inhibited p47phox induction in those treated with 40 μg/cm$^2$ silica (FIGS. 3C and 3D).

For the results shown in FIG. 3A, 3C, cell lysates were analyzed by Western blot using anti-p47phox and anti-actin Abs. For the results shown in FIGS. 3B and 3D, densitometric analysis of band intensity representing the mean±SE of three independent experiments. *, $p<0.05$, **, $p<0.01$.

FIGS. 4A-4D are bar graphs illustrating the effect of suppressive ODN on silica-mediated macrophage death. Silica-mediated cellular toxicity was assessed using MTT and LDH releases assays. RAW264.7 cells (FIGS. 4A and 4B) or freshly isolated peritoneal macrophages (FIGS. 4C and 4D) were cultured with 40 μg/cm$^2$ silica±3 μM ODN for 24 hours. Results show the mean percent viability (FIGS. 4A and 4C) and fold increase over background LDH levels (FIGS. 4B and 4D)±SE from three independent experiments. *, $p<0.05$, **, $p<0.01$.

Figure 5B:
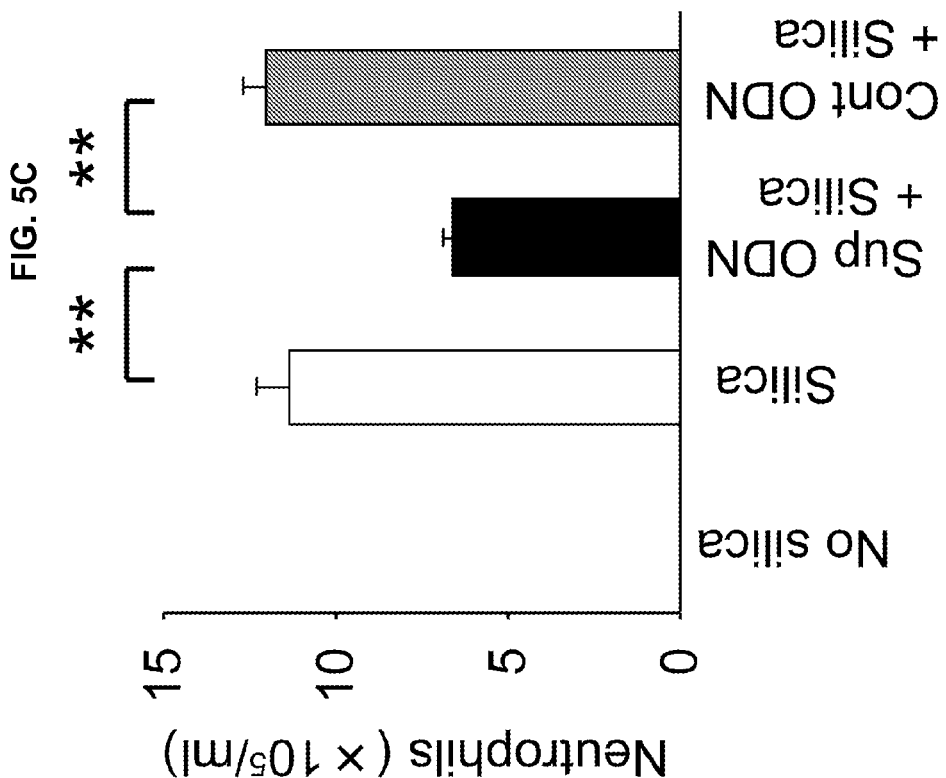
Figure 5C:
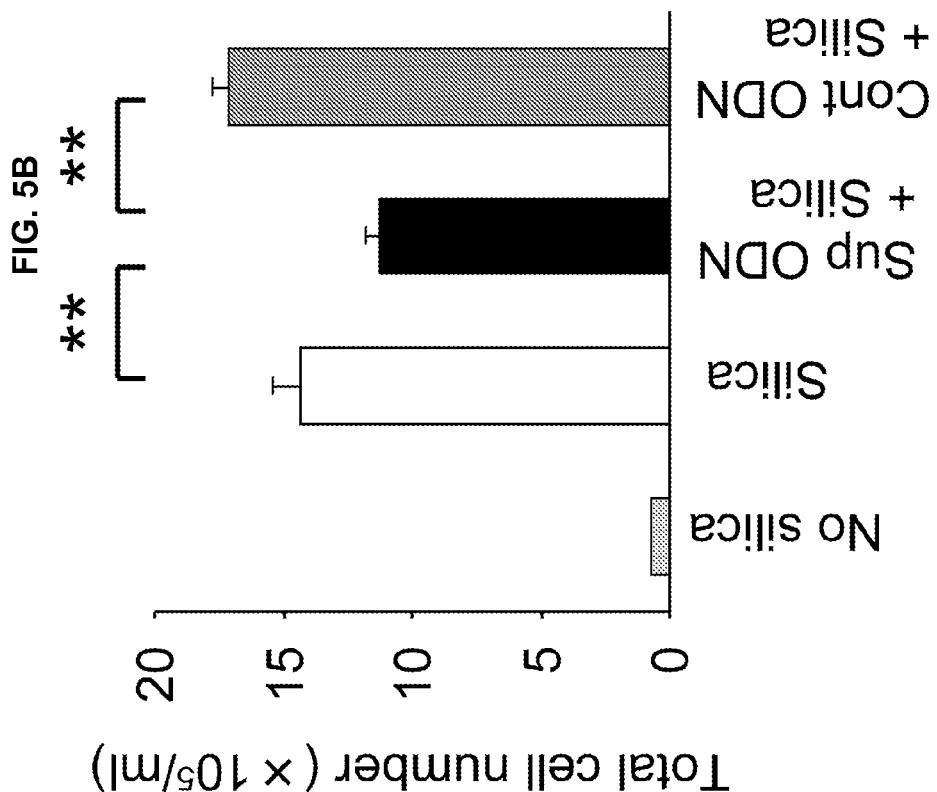

FIGS. 5A-5C are digital images and bar graphs showing the effect of suppressive ODN on silica-induced pulmonary inflammation. Mice were injected i.p. with 300 μg of ODN 24 and 3 hours before intra-tracheal instillation of 1 or 2.5 mg of silica particles. FIG. 5A is a set of photomicroscopic images of bronchoalveolar lavage cells collected 3 days after silica instillation and stained with Diff-Quick (magnification × 600). FIG. 5B is a bar graph of total cellularity and FIG. 5C is a bar graph of the neutrophil content of bronchoalveolar lavage fluid three days after mice were exposed to 2.5 mg of silica particles. Results represent the mean±SE of 2-3 independent experiments involving a total 6-9 mice/group. **, $p<0.01$.

Figure 6:
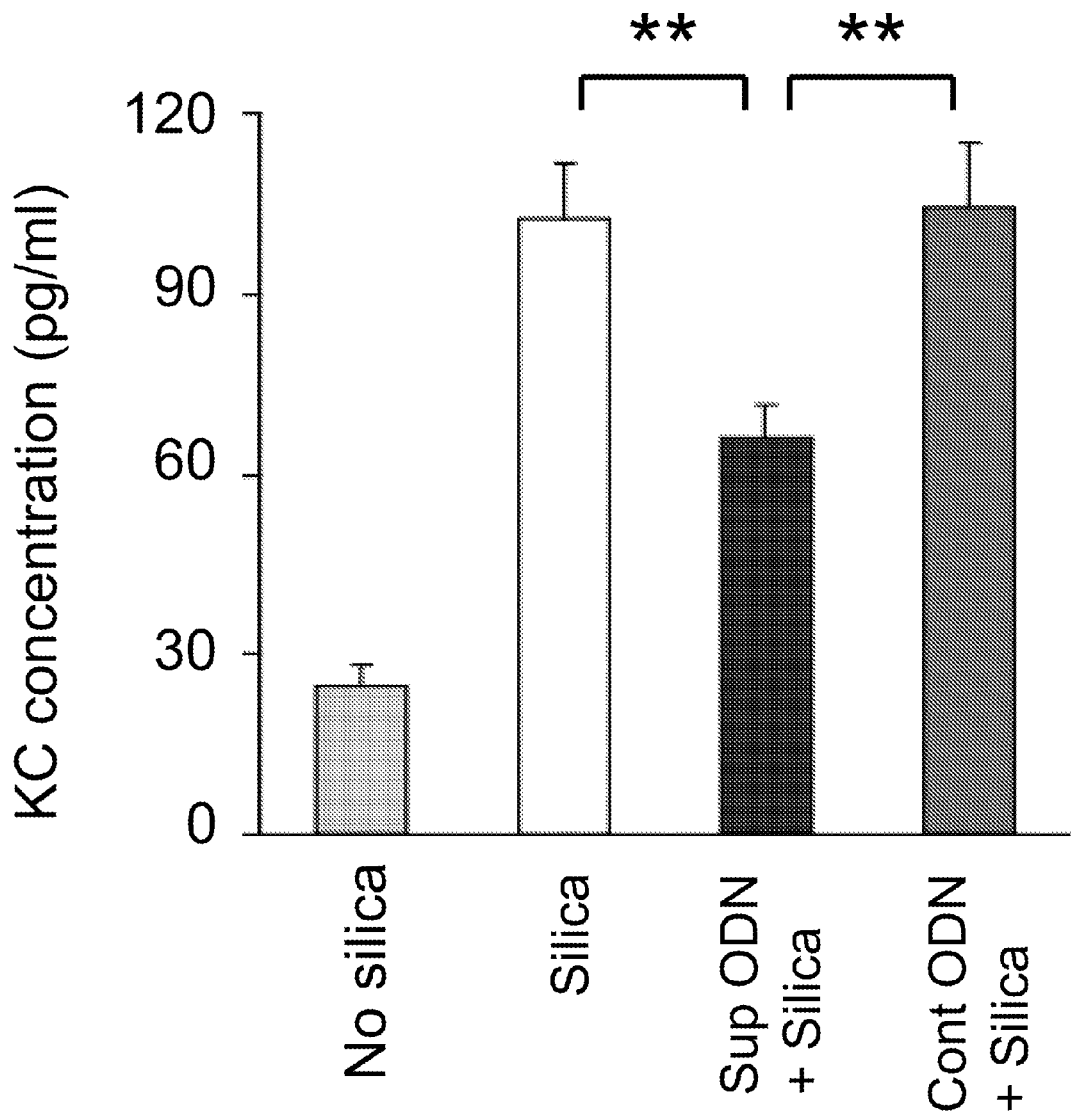

FIG. 6 is a bar graph showing the effect of suppressive ODN on silica-induced KC production in the lungs. Mice were treated as described in FIG. 5. The concentration of KC in BAL collected 3 days after silica exposure was determined by ELISA. Results represent the mean±SE from 2-3 independent experiments involving a total 5-8 mice/group. **, $p<0.01$.

Figure 7:
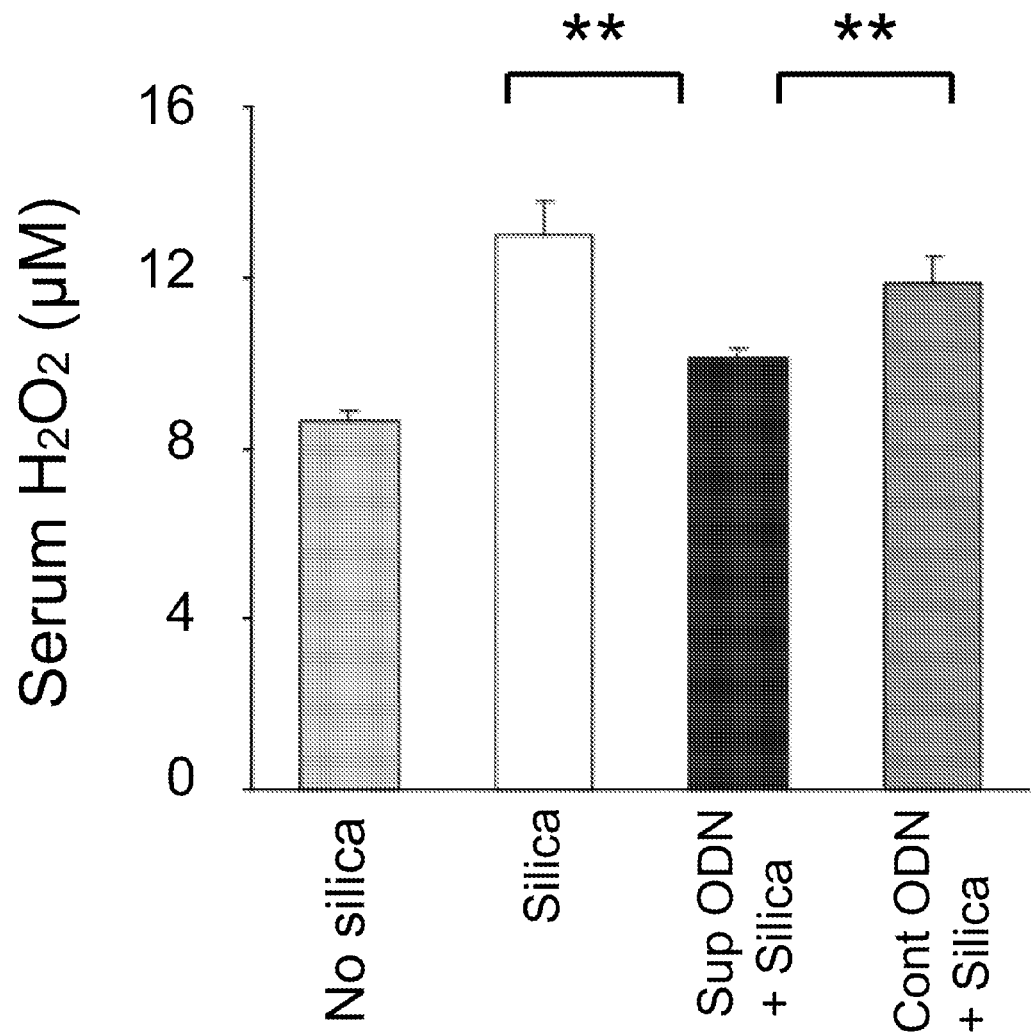

FIG. 7 is a bar graph showing the effect of Suppressive ODN on $H_2O_2$ production in vivo. BALB/c mice were treated as described in FIG. 5. $H_2O_2$ levels were measured using an $Fe^{3+}$-xylenol orange based assay. To insure that $H_2O_2$ concentration was monitored, background activity in catalase-treated samples was subtracted. Results represent the mean serum $H_2O_2$ concentration±SE from 2-3 independent experiments involving a total 5-10 mice/group. **, $p<0.01$.

Figure 8:
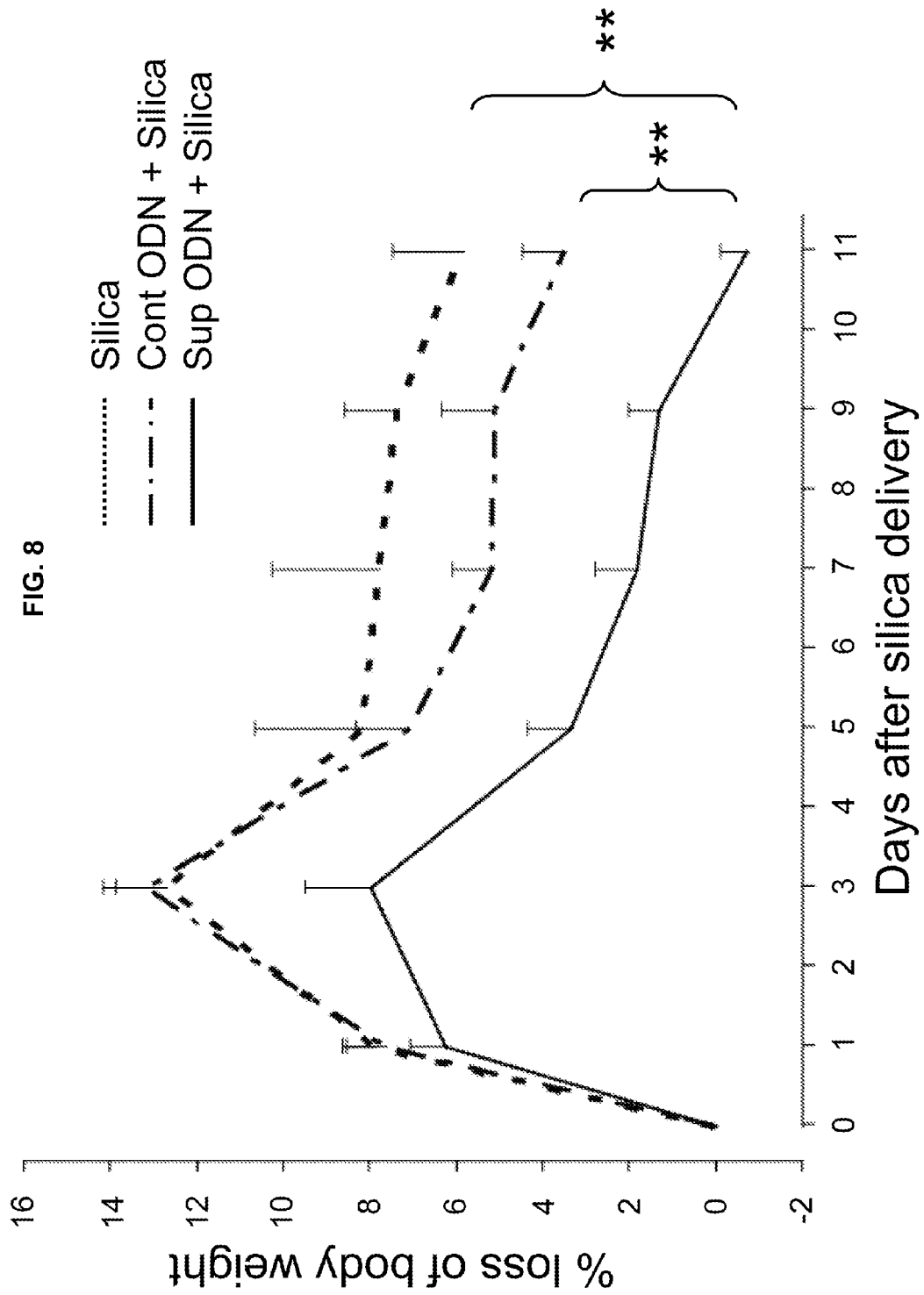

FIG. 8 is a line graph showing the effect of suppressive ODN on silica-induced weight loss. BALB/c mice (n=10/group) were treated as described in FIG. 5. The mean percent change in body weight±SE was determined for each animal at each time point. Statistic significance was analyzed by longitudinal regression analysis. **, $p<0.01$.

FIG. 9 is a line graph (survival curve) showing the effect of suppressive ODN on silica-induced mortality. BALB/c mice were treated as described in FIG. 5. Survival curves were analyzed by Kaplan-Meier statistics using the Log rank test. Data from two independent experiments involving 10-17 mice/group were combined to generate the survival curves. *, $p<0.05$, **, $p<0.01$.

SEQUENCE LISTING

The nucleic and amino acid sequences listed in the accompanying sequence listing are shown using standard letter abbreviations for nucleotide bases, and three letter code for amino acids, as defined in 37 C.F.R. 1.822. For double stranded nucleic acid molecules only one strand of each nucleic acid sequence is shown, but the complementary strand is understood as included by any reference to the displayed strand. The Sequence Listing is submitted as an ASCII text file (4239-81118-04 Sequence Listing.txt, 6.19 KB), which is incorporated by reference herein. In the accompanying sequence listing:

SEQ ID NOs: 1-25 are the nucleic acid sequence of exemplary suppressive ODNs (see Table 1 below).

SEQ ID NO: 26-28 are the nucleic acid sequence of control ODNs.

DETAILED DESCRIPTION

I. Abbreviations

| | |
|---|---|
| A: | adenine |
| Ab: | antibody |
| BAL: | bronchoalveolar lavage |
| BSA: | bovine serum albumin |

-continued

| | |
|---|---|
| C: | cytosine |
| CD: | circular dichroism |
| CpG ODN: | an oligodeoxynucleotide including a CpG motif. |
| DC: | dendritic cell |
| ELISA: | enzyme linked immunosorbant assay |
| FCS: | fetal calf serum |
| FEF 25-75: | forced expiratory flow determined over the midportion of a forced exhalation |
| FEV1: | forced expired volume in one second |
| FVC: | forced vital capacity |
| G: | guanine |
| hr: | hour |
| HRP: | horse radish peroxidase |
| IL: | interleukin |
| i.p.: | intraperitoneal |
| KC: | keratinocyte-derived cytokine |
| LDH; | lactase dehydrogenase |
| mAb: | monoclonal antibody |
| MIP-2: | macrophage inflammatory protein 2 |
| MTT: | 3-(4, 5-dimethylthiazol-2-yl)-2,5, diephenyltetraolium bromide |
| μg: | microgram |
| mm: | millimeter |
| mRNA: | messenger ribonucleic acid. |
| ODN: | oligodeoxynucleotide |
| NOX: | NADPH oxidase |
| Phox: | phagocytic oxidase |
| Pu: | purine |
| Py: | pyrimidine |
| ROS: | reactive oxygen species |
| T: | thymine |
| TNFα: | tumor necrosis factor alpha |

II. Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

Animal: Living multi-cellular vertebrate organisms, a category that includes, for example, mammals and birds. The term mammal includes both human and non-human mammals. Similarly, the term "subject" includes both human and veterinary subjects. Therefore, the general term "subject" is understood to include all animals, including, but not limited to, humans, or veterinary subjects, such as other primates, dogs, cats, horses, and cows.

Anti-Inflammatory Agent: Any of various medications that decrease the signs and symptoms (for example, pain, swelling, or shortness of breath) of inflammation. Corticosteroids are exemplary potent anti-inflammatory medications. Non-steroidal anti-inflammatory agents are also effective exemplary anti-inflammatory agents and do not have the side effects that can be associated with steroid medications.

Asbestosis: A pathological consequence of long-term inhalation of asbestos fibers. The primary symptom of asbestosis is generally the slow onset of shortness of breath on exertion. In severe, advanced cases, this may lead to respiratory failure. Coughing is not usually a typical symptom, unless the patient has other, concomitant respiratory tract diseases. People with extensive occupational exposure to the mining, manufacturing, handling or removal of asbestos are at risk of developing asbestosis. There is also an increased risk of lung cancer and mesothelioma with asbestos exposure. Asbestosis and lung cancer require prolonged exposure to asbestos. However, cases of mesothelioma have been documented with even 1-3 months of exposure, and only indirect exposure (through air ventilation system.) Most cases of asbestosis do not present until 5-10 years after exposure to the material.

Asbestosis is the scarring of lung tissue (around terminal bronchioles and alveolar ducts) resulting from the inhalation of asbestos fibers. There are two types of fibers, amphibole (thin and straight) and serpentine (curved). The former are primarily responsible for human disease as they are able to penetrate deeply into the lungs. When such fibers reach the alveoli (air sacs) in the lung, where oxygen is transferred into the blood, the foreign bodies (asbestos fibers) cause the activation of the lung's local immune system and provoke an inflammatory reaction.

Asbestosis presents as a restrictive lung disease. The total lung capacity (TLC) may be reduced through alveolar wall thickening. In the more severe cases, the drastic reduction in lung function due to the stiffening of the lungs and reduced TLC may induce right-sided heart failure (cor pulmonale). More than 50% of people affected with asbestosis develop plaques in the parietal pleura, in the space between the chest wall and lungs. Clinically, patients present with dry inspiratory crackles, clubbing of the fingers, and a diffuse fibrotic pattern in the lower lung lobes (where asbestosis is most prevalent).

Berylliosis: A lung disease caused by beryllium exposure in industries such as, but not limited to, the aeorospace industry or in the manufacture of fluorescent light bulbs. With single or prolonged exposure by inhalation, the lungs become hypersensitive to beryllium causing the development of small inflammatory nodules, called granulomas. The onset of symptoms can range from weeks up to tens of years from the initial exposure. In some individuals a single exposure can cause berylliosis. Ultimately, this process leads to restrictive lung disease, a decreased diffusion capacity. Clinically patients experience cough and shortness of breath. Other symptoms include chest pain, joint aches, weight loss and fever.

Bronchodilator: An antispasmodic or other agent that dilates a bronchus or bronchiole. Bronchodilators relax the smooth muscles of the airways, allowing the airway to dilate. Bronchodilator medicines do not counteract inflammation, Bronchodilators can be used to treat the symptoms of a pneumoconiosis, such as asbestosis or silicosis, although they do not treat the underlying pathology.

Bronchiolitis obliterans: A disease initiated by inhalation of particles (inorganic dust, organic dust, and a combination thereof) in the small conducting airways of the respiratory tract. Inflammation of these airways ultimately results in irreversible airway obstruction. Silo workers, textile workers, and workers in the food industry (for example, food-flavoring and microwave popcorn packaging) can develop this type of bronchiolitis through the inhalation of particles.

CD Value: The formation of G-tetrads yields a complex with different physical properties than the individual oligonucleotides. Spectroscopically, this is manifested by an increase in circular dichroism (CD), and an increase in peak absorbance to the 260-280 nm wavelength owing to the formation of secondary structures. In on embodiment, a method for identifying oligonucleotides that form G-tetrads is to assess the CD values. An increase in peak ellipticity values to greater than 2.0 is typical of a G-tetrad forming oligonucleotide. The higher the ellipticity value, the greater the tetrad-forming capacity of the oligonucleotide.

Chemokine: A type of cytokine (a soluble molecule that a cell produces to control reactions between other cells) that specifically alters the behavior of leukocytes (white blood cells). Examples include, but are not limited to, interleukin 8 (IL-8), platelet factor 4, melanoma growth stimulatory protein, etc.

Cytokine: The term "cytokine" is used as a generic name for a diverse group of soluble proteins and peptides that act as humoral regulators at nano- to picomolar concentrations and which, either under normal or pathological conditions, modulate the functional activities of individual cells and tissues. These proteins also mediate interactions between cells directly and regulate processes taking place in the extracellular environment. Examples of cytokines include, but are not limited to, tumor necrosis factor α (TNFα), interleukin-6 (IL-6), interleukin-10 (IL-10), interleukin-12 (IL-12), macrophage inflammatory protein 2 (MIP-2), KC, and interferon-γ(INF-γ).

Enzyme: Any of numerous proteins or conjugated proteins produced by living organisms and functioning as biochemical catalysts.

Expectorant: A drug or chemical substance that induces the ejection of mucus, phlegm, and other fluids from the lungs and air passages, for example by coughing.

Expiratory Flow Rate: The rate at which air is expelled from the lungs during exhalation. A subject's maximum expiratory flow is measured by a simple pulmonary test; in performing the test, a subject first takes as deep a breath as possible, then exhales as rapidly and as completely as possible into a machine known as a spirometer, which measures the rate of exhalation. Forced expiratory flow 25-75 (FEF 25-75) is a measurement of the forced expiratory flow determined over the midportion of a forced exhalation. An increase in the forced expiratory flow (FEF) or FEF 25-75 reflects a decrease in bronchoconstriction and an improvement in pulmonary function.

Forced Expiratory Volume (FEV): The forced expiratory volume is the volume of air resulting from the forced expiratory flow test in which a subject first inspires maximally to the total lung capacity, then exhales as rapidly and as completely as possible. The forced expired volume in one second (FEV1) represents the maximum expiratory air volume a subject can produce during a one-second interval. An increase in FEV or FEV1 reflects a decrease in bronchoconstriction and an improvement in pulmonary function.

Forced Vital Capacity (FVC): The volume of air resulting from the forced expiratory flow test in which a subject first inspires maximally to the total lung capacity, then exhales as rapidly and as completely as possible. An increase in FVC reflects a decrease in bronchoconstriction and an improvement in pulmonary function.

G-tetrad: G-tetrads are G-rich DNA segments that can accommodate complex secondary and/or tertiary structures (see FIG. 1). A G-tetrad involves the planar association of four Gs in a cyclic Hoogsteen hydrogen bonding arrangement (this involves non-Watson Crick base-pairing). In general, either a run of four or more contiguous Gs or a hexameric region in which >50% of the bases are Gs, is needed for an ODN to form a G-tetrad. The longer the run of contiguous Gs, and the higher the G content of the ODN, the higher the likelihood of G-tetrad formation, as reflected by higher CD or ellipticity values.

Oligonucleotides that form G-tetrads can also form higher-level aggregates that are more easily recognized and taken up by immune cells, for example, through scavenger receptors or by nucleolin.

Guanosine-Rich Sequence: A hexameric region of a nucleotide sequence in which >50% of the bases are Gs.

Immune Response: A response of a cell of the immune system, such as a B cell or T cell to a stimulus. In one embodiment, the response is an inflammatory response.

Immunostimulatory CpG Motifs: Immunostimulatory sequences that trigger macrophages, monocytes and lymphocytes to produce a variety of pro-inflammatory cytokines and chemokines. CpG motifs are found in bacterial DNA. The innate immune response elicited by CpG DNA reduces host susceptibility to infectious pathogens, and can also trigger detrimental inflammatory reactions. Immunostimulatory CpG motifs are found in "D" and "K" type ODNs (see, for example PCT Publication No. WO 01/51500, published on Jul. 19, 2001).

Infiltration: The diffusion or accumulation of a substance, such as a neutrophil, in a tissue or cell.

Inflammatory Response: An accumulation of white blood cells, either systemically or locally at the site of inflammation. The inflammatory response may be measured by many methods well known in the art, such as the number of white blood cells (WBC), the number of polymorphonuclear neutophils (PMN), a measure of the degree of PMN activation, such as luminal enhanced-chemiluminescence, or a measure of the amount of cytokines present.

Inspiratory Flow Rate: The rate at which air travels into the lungs during inspiration. Inspiratory flow is measured by a simple pulmonary test; in performing the test the subject takes as deep and rapid a breath as possible from a machine known as a spirometer, which measures the rate of inspiration. An increase in inspiratory flow rate reflects a decrease in bronchoconstriction and an improvement in pulmonary function.

Isolated: An "isolated" biological component (such as a nucleic acid, peptide or protein) has been substantially separated, produced apart from, or purified away from other biological components in the cell of the organism in which the component naturally occurs, i.e., other chromosomal and extrachromosomal DNA and RNA, and proteins. Nucleic acids, peptides and proteins which have been "isolated" thus include nucleic acids and proteins purified by standard purification methods. The term also embraces nucleic acids, peptides and proteins prepared by recombinant expression in a host cell as well as chemically synthesized nucleic acids.

Leukocyte: Cells in the blood, also termed "white cells," that are involved in defending the body against infective organisms and foreign substances. Leukocytes are produced in the bone marrow. There are five main types of white blood cells, subdivided into two main groups: polymorphonuclear leukocytes (neutrophils, eosinophils, basophils) and mononuclear leukocytes (monocytes and lymphocytes). When an infection is present, the production of leukocytes increases.

Leukotriene Antagonist/Leukotriene Formation Inhibitor: Drugs that block the effects of leukotrienes (leukotriene antagonists) or inhibit the formation of leukotrienes (leukotriene formation inhibitors). Leukotrienes are substances that are associated with an allergic response and inflammation. In the airways, they cause bronchial or alveolar narrowing and increase secretions. Drugs can interfere with leukotriene action by inhibiting their synthesis (for example, zileuton, ZYFLO®, Abbott Laboratories) or blocking the receptor to which they bind (for example, monteleukast, SINGULAIR®, Merck and Company, and others). If a pneumoconisis is complicated by allergic reactions in the lung than leukotirene antgonists/leukotriene formation inhibitors can be sued in a treatment regimen.

Lung Volume: The maximum volume the lungs can hold.

Macrophage: A monocyte that has left the circulation and settled and matured in a tissue. Macrophages are found in large quantities in the spleen, lymph nodes, alveoli, and tonsils. About 50% of all macrophages are found in the liver as Kupffer cells. They are also present in the brain as microglia, in the skin as Langerhans cells, in bone as osteoclasts, as well as in seous cavities and breast and placental tissue.

Along with neutrophils, macrophages are the major phagocytic cells of the immune system. They have the ability to recognize and ingest foreign antigens through receptors on the surface of their cell membranes; these antigens are then destroyed by lysosomes. Their placement in the peripheral lymphoid tissues enables macrophages to serve as the major scavengers of the blood, clearing it of abnormal or old cells and cellular debris as well as pathogenic organisms. Macrophages also serve a vital role by processing antigens and presenting them to T cells, activating the specific immune response. They also release many chemical mediators that are involved in the body's defenses, including interleukin-1.

Mast Cell Stabilizer: A class of anti-inflammatory agents that work by preventing the release of substances in the body that cause inflammation. This is done by controlling the release of histamine from a white blood cells called mast cells. Examples include cromolyn and nedocromil.

Nucleic Acid: A deoxyribonucleotide or ribonucleotide polymer in either single or double stranded form, and unless otherwise limited, encompasses known analogues of natural nucleotides that hybridize to nucleic acids in a manner similar to naturally occurring nucleotides.

Occupational Lung Disease: A specific branch of occupational diseases concerned primarily with work related exposures to harmful substances, such as dusts or gases, and the subsequent pulmonary disorders that may occur as a result.

Oligonucleotide or "oligo": Multiple nucleotides (i.e., molecules comprising a sugar (e.g., ribose or deoxyribose) linked to a phosphate group and to an exchangeable organic base, which is either a substituted pyrimidine (Py) (e.g., cytosine (C), thymine (T) or uracil (U)) or a substituted purine (Pu) (e.g., adenine (A) or guanine (G)). The term "oligonucleotide" as used herein refers to both oligoribonucleotides (ORNs) and oligodeoxyribonucleotides (ODNs). The term "oligonucleotide" also includes oligonucleosides (i.e., an oligonucleotide minus the phosphate) and any other organic base polymer. Oligonucleotides can be obtained from existing nucleic acid sources (e.g., genomic or cDNA), but are preferably synthetic (i.e., produced by oligonucleotide synthesis).

A "stabilized oligonucleotide" is an oligonucleotide that is relatively resistant to in vivo degradation (for example via an exo- or endo-nuclease). In one embodiment, a stabilized oligonucleotide has a modified phosphate backbone. One specific, non-limiting example of a stabilized oligonucleotide has a phophorothioate modified phosphate backbone (wherein at least one of the phosphate oxygens is replaced by sulfur). Other stabilized oligonucleotides include: nonionic DNA analogs, such as alkyl- and aryl-phosphonates (in which the charged phosphonate oxygen is replaced by an alkyl or aryl group), phophodiester and alkylphosphotriesters, in which the charged oxygen moiety is alkylated. Oligonucleotides which contain a diol, such as tetraethyleneglycol or hexaethyleneglycol, at either or both termini have also been shown to be substantially resistant to nuclease degradation.

An "oligonucleotide delivery complex" is an oligonucleotide associated with (e.g., ionically or covalently bound to; or encapsulated within) a targeting means (e.g., a molecule that results in a higher affinity binding to a target cell (e.g., B-cell or natural killer (NK) cell) surface and/or increased cellular uptake by target cells). Examples of oligonucleotide delivery complexes include oligonucleotides associated with: a sterol (e.g., cholesterol), a lipid (e.g., cationic lipid, virosome or liposome), or a target cell specific binding agent (e.g., a ligand recognized by a target cell specific receptor). Preferred complexes must be sufficiently stable in vivo to prevent significant uncoupling prior to internalization by the target cell. However, the complex should be cleavable or otherwise accessible under appropriate conditions within the cell so that the oligonucleotide is functional. (Gursel, *J. Immunol.* 167: 3324, 2001).

Parenteral: Administered outside of the intestine, e.g., not via the alimentary tract. Generally, parenteral formulations are those that will be administered through any possible mode except ingestion. This term especially refers to injections, whether administered intravenously, intrathecally, intramuscularly, intraperitoneally, intraarticularly, or subcutaneously, and various surface applications including intranasal, intradermal, and topical application, for instance.

Particles or Inhaled Particles: Organic particulate matter (e.g., organic dust as known in the art), inorganic particulate matter (e.g., inorganic dust), or a combination thereof, the particulate matter capable of being inhaled by an individual, and capable of inducing inflammation once inhaled by the individual. Inorganic particulate matter is well known in the art to include, but is not limited to, pulverized concrete, fiberglass, asbestos, silica, cristobalite, man-made vitreous fibers, and a combination thereof.

Pharmaceutical Agent or Drug: A chemical compound or composition capable of inducing a desired therapeutic or prophylactic effect when properly administered to a subject. Pharmaceutical agents include, but are not limited to, anti-infective agents, anti-inflammatory agents, bronchodilators, enzymes, expectorants, leukotriene antagonists, leukotriene formation inhibitors, and mast cell stabilizers.

Pharmaceutically Acceptable Carriers: The pharmaceutically acceptable carriers useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of the suppressive ODNs herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

P47-phox: One enzyme in a complex of enzymes that produces reactive oxygen species. The two cytosolic components of the NADPH oxidase complex are p47-phox and p67-phox. P47-phox has an SH3 domains that may interact with the cytoskeleton. When a phagocytic cell is activated by opsonized pathogen or other stimuli, the subunits of the NADPH oxidase complex translocate and form a complex that eventually produces the superoxide radical ($O_2^-$). An exemplary amino acid sequence of p47-phox can be found as GENBANK® Accession No. AAB95193, Jan. 7, 1998, herein incorporated by reference.

Pneumoconiosis: Lung disease caused by the inhalation of dust or particles. Substances known to cause pneumoconiosis include coal dust, asbestos, and silica which is usually in the form of quartz) and barium. The physical state of the agent is of importance; particles are deposited in the respiratory tract as the result of sedimentation, inertial impaction and diffusion. Examples include asbestosis, silicosis and beryllosis. The amount of dust retained depends on three variables: (1) concentration in the air; (2) duration of exposure; and (3) the effectiveness of clearance. Over 80% of large particles (about 6 µm in diameter or greater) are filtered out in the vibrassae of the nares, or, after impaction in the linings of the nasal passages or larger airways, are removed by mucociliary clearance. Very small particles (less than about 0.5 µm in diameter or less) can remain suspended in the air and be exhaled. However, intermediate particles (about 1 to about 5 µm in diameter) can penetrate to the respiratory bronchioles and air spaces. In addition, asbestos fibers, which are up to about 100 µm in length, can remain suspended in moving air columns and penetrate to the respiratory bronchioles and alveoli and can cause pneumoconiosis. Smaller particles in the range of about 2 µm or less are likely to cause damage primarily within the alveoli. Generally, the larger the particle, the more proximal the deposition within the lung. Larger particles, such as silica particles can evoke fibrosing collagenous pneumoconiosis.

Preventing or Treating a Disease: Inhibiting a disease refers to inhibiting the full development of a disease, for example in a person who is at risk for a disease such as asbestosis or silicosis. An example of a person at risk for asbestosis or silicosis is someone exposed to silica dust or asbestos Inhibiting a disease process includes preventing the development of the disease. "Treatment" refers to a therapeutic intervention that ameliorates a sign or symptom of a disease or pathological condition, such as after it has begun to develop.

Reactive Oxygen Species: Oxygen ions, free radicals, and peroxides, both inorganic and organic. They are generally very small molecules and are highly reactive due to the presence of unpaired valence shell electrons. ROS form as a natural byproduct of the normal metabolism of oxygen and have important roles in cell signaling. However, during times of environmental stress ROS levels can increase dramatically, which can result in significant damage to cell structures. This cumulates into a situation known as oxidative stress. They are also generated by exogenous sources such as ionizing radiation.

The effects of ROS on cell metabolism have been well documented in a variety of species. These include not only roles in apoptosis (programmed cell death), but also positive effects such as the induction of host defense genes and mobilisation of ion transport systems. This is implicating them more frequently with roles in redox signaling or oxidative signaling. Generally, harmful effects of reactive oxygen species on the cell are most often damage of DNA, oxidations of polydesaturated fatty acids in lipids, oxidations of amino acids in proteins, and oxidatively inactivate specific enzymes by oxidation of co-factors.

Silicosis: A fribrogenic pneumoconiosis caused by inhaling crystalline free silica (quartz) dust characterized by discrete nodular pulmonary fibrosis, and in more advance stages, by conglmerate fibrosis and respiratory impairment. Silicosis follows long-term inhalation of small particles of crystalline silica (silicon dioxide) in such industries as metal mining, foundries, pottery making and sandstone and granite cutting. Silicosis (also known as Grinder's disease and Potter's rot) is marked by inflammation and scarring in forms of nodular lesions in the upper lobes of the lungs. Silicosis (especially the acute form) is characterized by shortness of breath, fever, and cyanosis (bluish skin). It may often be misdiagnosed as pulmonary edema (fluid in the lungs), pneumonia, or tuberculosis.

Symptoms of silicosis include: tachypnea or shortness of breath after physical exertion; dry or severe cough, often persistent and accompanied by hoarseness of the throat; fatigue or tiredness; changes in breathing pattern (rapid breathing or shallow breathing); loss of appetite; chest pain; fever; gradual dark shallow rifts in nails eventually leading to cracks. In advanced cases, cyanosis, cor pulmonale; and respiratory insufficiency can occur. Patients with silicosis are particularly susceptible to tuberculosis (TB) infection.

There are several types of silicosis in humans. "Chronic silicosis" occurs after 15-20 years of exposure to moderate to low levels of silica dust. Chronic silicosis itself is further subdivided into simple and complicated silicoses. "Asymptomatic silicosis" is an early case of the disease wherein the subject presents with exposure by without any symptoms. "Accelerated silicosis" develops 5-10 years after high exposure to silica dust. Symptoms include severe shortness of breath, weakness, and weight loss. "Acute silicosis" develops a few months to two years after exposure to very high concentrations of silica dust. Symptoms of acute silicosis include severe disabling shortness of breath, weakness, and weight loss, often leading to death. In mice, acute silicosis develops over a period of days or weeks upon exposure to silica particles Suppressive ODN: DNA molecules of at least eight nucleotides in length, such as about 8 to about 40 nucleotides in length or about ten to about 30 nucleotides in length, wherein the oligodeoxynucleotide has at least four guanosines, and has a CD value of greater than about 2.9 and suppresses an immune response in a subject, such as an immune response associated with the development of pneumoconiosis in a subject. Generally, a suppressive ODN has at least four guanonsines. In additional embodiment, a suppressive ODN includes repeats of the nucleic acid sequence TTAGGG. Exemplary suppressive ODN are described below. In one embodiment, a suppressive ODN inhibits the generation of reactive oxygen intermediates, such as by macrophages.

Therapeutic Agent: Used in a generic sense, it includes treating agents, prophylactic agents, and replacement agents.

Therapeutically Effective Amount: A quantity of a specified compound or ODN sufficient to achieve a desired effect in a subject being treated. For instance, this can be the amount of a suppressive ODN necessary to suppress CpG-induced immune cell activation in a subject, or a dose sufficient to prevent advancement, or to cause regression of a disease, or which is capable of relieving symptoms caused by a disease, such as pain, mesothelioma, silicosis, asbestosis, beryllosis, fluid accumulation, or shortness of breath.

A therapeutically effective amount of a suppressive ODN can be administered systemically or locally. In addition, an effective amount of a suppressive ODN can be administered in a single dose, or in several doses, for example daily, during a course of treatment. However, the effective amount of the ODN will be dependent on the preparation applied, the subject being treated, the severity and type of the affliction, and the manner of administration of the compound. For example, a therapeutically effective amount of a suppressive ODN can vary from about 0.01 mg/kg body weight to about 1 g/kg body weight in some specific, non-limiting examples, or from about 0.01 mg/kg to about 60 mg/kg of body weight, based on efficacy.

The suppressive ODNs disclosed herein have equal applications in medical and veterinary settings. Therefore, the general term "subject" is understood to include all animals, including, but not limited to, humans or veterinary subjects, such as other primates, dogs, cats, horses, and cows.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Description of Several Embodiments

A. Suppressive Oligodeoxynucleotides and Guanosine-Quadruplexes (G-Tetrads)

The present disclosure relates to the use of a class of DNA motifs that selectively inhibits or suppresses immune activation. Optimal activity is observed using multimers of these motifs, which are rich in G bases. The suppressive ODNs of the disclosure are highly specific (i.e., are neither toxic nor non-specifically immunosuppressive), and are useful for inhibiting an immune response. In one embodiment, a suppressive ODN is of use for treating occupational lung inflammation, such as asbestosis, silicosis, or berryliosis. In other embodiments a suppressive ODN is of use for preventing mesotheliomas. In a further embodiment, a suppressive ODN is of use for inhibiting the generation of reactive oxygen intermediates, such as by macrophages.

In some embodiments, the ODNs of use in the methods disclosed herein are capable of forming G-quadruplexes (G-tetrads). G-tetrads are G-rich DNA segments that can accommodate complex secondary and/or tertiary structures (see FIG. 1 of U.S. Patent Publication No. US-2004-0132682-A1, herein incorporated by reference). A G-tetrad involves the planar association of four Gs in a cyclic Hoogsteen hydrogen bonding arrangement (this involves non-Watson Crick base-pairing). In general, either a run of two or more contiguous Gs or a hexameric region in which >50% of the bases are Gs, is needed for an ODN to form a G-tetrad. The longer the run of continuous Gs, and the higher the G content of the ODN, the higher the likelihood of G-tetrad formation, as reflected by higher ellipticity values. Oligonucleotides that form G-tetrads can also form higher-level aggregates that are more easily recognized and taken up by immune cells, for example, through scavenger receptors or by nucleolin.

The CD value is an increase in peak absorbance to the 260-280 nm wavelength, generally owing to the formation of secondary structures. Thus, a convenient method for identifying suppressive oligonucleotides is to study their CD values. An increase in peak ellipticity values to greater than 2.0 is typical of a suppressive oligonucleotide, such as a ODN with at least four guanosines.

In some embodiments, suppressive ODNs can have CD values of about 2.2, 2.4, 2.6, 2.8, 3.0, 3.2, 3.5, 4.0, 4.5, 5.0, 5.5, 6.0, 6.5, 7.0, 7.5, 8.0, 8.5, 9.0, or higher. The higher the ellipticity value, the greater the tetrad-forming capacity of the oligonucleotide, so an ODN with a CD value of 8.5 is typically more suppressive than an ODN with a CD value of 2.9. Generally, a suppressive ODN includes at least four guanosines. In some embodiments, the ODN forms a G-tetrad.

In some embodiments, the ODN is from about 8 to about 100 nucleotides in length. In particular examples, the ODN is from about 8 to about 40 nucleotides in length, or from about 10 to about 30 nucleotides in length such as 18, 20, 22, 24, 26, or 28 nucleotides in length. Optionally, the suppressive ODN has multiple guanosine-rich sequences, for example, in certain embodiments the ODN has from about two to about 20 guanosine-rich sequences, or, more particularly, from about two to about four guanosine-rich sequences. In some embodiments, the suppressive ODN is 18, 24 or 30 nucleotides in length.

In one embodiment, the suppressive ODNs have a sequence comprising at least one of the human telomere-derived TTAGGG suppressive motifs. In some examples, the ODN has at least one TTAGGG motif, and in certain examples, the ODN has multiple TTAGGG motifs. For example, in particular embodiments, the ODN has from about two to about 20 TTAGGG motifs. In this context, "about" refers to a difference of an integer amount. Thus, in some examples, the suppressive ODNs have from two to five TTAGGG motifs, such as three or four TTAGGG motifs. In some embodiments, the ODN includes or consists of three, four, five, six, seven, eight, nine, ten, eleven, twelve, thirteen, fourteen or fifteen TTAGGG motifs. Single TTAGGG motifs are suppressive only when incorporated into larger ODNs with greater than 10 bases. In several examples, the suppressive ODN is from about 18 to about 30 nucleotides in length and includes three or four TTAGGG motifs.

Suppression of a pneumoconiosis, such as silicosis, berryliosis or asbestosis requires a G-tetrad-forming sequence that imposes the two-dimensional structure necessary for G-tetrad formation. Examples of suppressive ODN include, but are not limited to, those shown in Table 1. However, any oligonucleotide capable of forming G-tetrads may be used to suppress CpG DNA-induced immune activation. In particular examples, the ODN has a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, and SEQ ID NO: 25 (see Table 1). Combinations of these ODNs are also of use in the methods disclosed herein. Thus, two, three, four, five, six, seven, eight, nine or more than ten of the oligodeoxynucleotides can be administered to a subject. These ODNs can be administered as parts of a single nucleotide molecule, or on different nucleotide molecules.

TABLE 1

List of suppressive ODNs (and controls)

| # | Name | SEQ ID | Sequence |
|---|------|--------|----------|
| 1 | A151 | SEQ ID NO: 1 | (TTAGGG)$_4$ (ie-4 repeats of the TTAGGG base sequence) |
| 2 | A152 | SEQ ID NO: 2 | (TTAGGG)$_3$ |
| 3 | A153 | SEQ ID NO: 3 | (TTAGGG)$_2$ |
| 4 | A156 | SEQ ID NO: 4 | (TGGGCGGT)$_3$ |
| 5 | A157 | SEQ ID NO: 5 | (TGGGCGGT)$_2$ |
| 6 | A1 | SEQ ID NO: 6 | TCAACCTTCATTAGGG |
| 7 | A161 | SEQ ID NO: 7 | TTAGGGTTAGGGTCAACCTTCA |
| 8 | A162 | SEQ ID NO: 8 | TCAACCTTCATTAGGGTTAGGG |
| 9 | A163 | SEQ ID NO: 9 | GGGTTAGGGTTATCAACCTTCA |
| 10 | A164 | SEQ ID NO: 10 | TCAACCTTCAGGGTTAGGGTTA |
| 11 | A15 | SEQ ID NO: 11 | GGGTGGGTGGGTATTACCATTA |
| 12 | A16 | SEQ ID NO: 12 | ATTACCATTAGGGTGGGTGGGT |
| 13 | A17 | SEQ ID NO: 13 | TGGGCGGTTCAAGCTTGA |
| 14 | A18 | SEQ ID NO: 14 | TCAAGCTTCATGGGCGGT |
| 15 | A19 | SEQ ID NO: 15 | GGGTGGGTGGGTAGACGTTACC |
| 16 | A20 | SEQ ID NO: 16 | GGGGGGTCAAGCTTCA |
| 17 | A21 | SEQ ID NO: 17 | TCAAGCTTCAGGGGGG |
| 18 | A22 | SEQ ID NO: 18 | GGGGGGTCAACGTTCA |
| 19 | H154 | SEQ ID NO: 19 | CCTCAAGCTTGAGGGG |
| 20 | 1502 | SEQ ID NO: 20 | GAGCAAGCTGGACCTTCCAT |
| 21 | 1502(7DG) | SEQ ID NO: 26 | GAGCAAGCTG*G*ACCTTCCAT |
| 22 | 1502-1555 | SEQ ID NO: 21 | GAGCAAGCTGGTAGACGTTAG |
| 23 | 1502-1555(7DG) | SEQ ID NO: 27 | GAG*CAAGCTG*GTAGACGTTAG |
| 24 | 1502-1555(7DG) | SEQ ID NO: 28 | G*AGCAAGCTG*GTAGACGTTAG |
| 25 | 1503 | SEQ ID NO: 22 | GGGCAAGCTGGACCTGGGGG |
| 26 | 1504 | SEQ ID NO: 23 | GGGGAAGCTGGACCTGGGGG |
| 27 | 1505 | SEQ ID NO: 24 | GGGCAAGCTGGACCTTCGGG |
| 28 | 1506 | SEQ ID NO: 25 | GGCAAGCTGGACCTTCGGGGG |

In the table above, G* indicates 7-deazaguanine. Due to the presence of 7-deazaguanine, ODN 21 (SEQ ID NO: 26) is an inactive form of ODN 20 (SEQ ID NO: 20), and ODNs 1502-155 (7DG) (SEQ ID NOs: 27 and 28, respectively) are inactive forms of ODN 1502-1555 (SEQ ID NO: 21).

Furthermore, in particular embodiments, the ODN is modified to prevent degradation. In one embodiment, suppressive ODNs can include modified nucleotides to confer resistance to degradation. Without being bound by theory, modified nucleotides can be included to increase the stability of a suppressive ODN. Thus, because phosphorothioate-modified nucleotides confer resistance to exonuclease digestion, the suppressive ODNs are "stabilized" by incorporating phosphorothioate-modified nucleotides.

In some embodiments, the ODN has a phosphate backbone modification, and in particular examples, the phosphate backbone modification is a phosphorothioate backbone modification. In one embodiment, the guanosine-rich sequence and its immediate flanking regions include phosphodiester rather than phosphorothioate nucleotides. In one specific non-limiting example, the sequence TTAGGG includes phosphodiester bases. In some examples, all of the bases in an ODN are phosphodiester bases. In other examples, the ODN is a phosphorothioate/phosphodiester chimera.

As disclosed herein, any suitable modification can be used to render the ODN resistant to degradation in vivo (such as resistant to degradation by an exo- or endo-nuclease). In one specific, non-limiting example, a modification that renders the ODN less susceptible to degradation is the inclusion of nontraditional bases such as inosine and quesine, as well as acetyl-, thio- and similarly modified forms of adenine, cytidine, guanine, thymine, and uridine. Other modified nucleotides include nonionic DNA analogs, such as alkyl or aryl phosphonates (i.e., the charged phosphonate oxygen is replaced with an alkyl or aryl group, as set forth in U.S. Pat. No. 4,469,863), phosphodiesters and alkylphosphotriesters (i.e., the charged oxygen moiety is alkylated, as set forth in U.S. Pat. No. 5,023,243 and European Patent No. 0 092 574). ODNs containing a diol, such as tetraethyleneglycol or hexaethyleneglycol, at either or both termini, have also been shown to be more resistant to degradation.

The suppressive ODNs of the disclosure can be synthesized by standard methods well known in the art. Most commonly, synthesis is performed on an oligonucleotide synthesizer using the standard cyanoethyl phosphoramidite chemistry. These include, but are not limited to, phosphodiester, phosphorothioate, peptide nucleic acids, synthetic peptide analogues, and any combination thereof. Those skilled in the art will recognize that any other standard technique may be used to synthesize the suppressive ODN described herein.

In one embodiment, a suppressive ODN is included in a delivery complex. The delivery complex can include the suppressive ODN and a targeting agent. Any suitable targeting agent can be used. For example, in some embodiments, a suppressive ODN is associated with (e.g., ionically or covalently bound to, or encapsulated within) a targeting means (e.g., a molecule that results in higher affinity binding to a target cell, such as a B cell). A variety of coupling or cross-linking agents can be used to form the delivery complex, such as protein A, carbodiamide, and N-succinimidyl-3-(2-pyridyldithio) propionate (SPDP). Examples of oligodeoxynucleotide delivery complexes include a suppressive ODN associated with a sterol (e.g., cholesterol), a lipid (e.g., a cationic lipid, anionic lipid, virosome or liposome), and a target cell specific binding agent (e.g., a ligand recognized by target cell specific receptor). Without being bound by theory, the complex is sufficiently stable in vivo to prevent significant uncoupling prior to delivery to the target cell. In one embodiment, the delivery complex is cleavable such that the ODN is released in a functional form at the target cells.

B. Pharmaceutical Compositions

The suppressive ODNs described herein may be formulated in a variety of ways. Pharmaceutical compositions are thus provided for both local (such as inhalational) use and for systemic (such as oral) use. Therefore, the disclosure includes within its scope pharmaceutical compositions comprising at least one suppressive ODN formulated for use in human or veterinary medicine. While the suppressive ODNs will typically be used to treat human subjects they may also be used to treat similar or identical diseases in other vertebrates, such other primates, dogs, cats, horses, and cows.

Pharmaceutical compositions that include at least one suppressive ODN as described herein as an active ingredient, or that include both a suppressive ODN and an additional respiratory agent. In several examples, the pharmaceutical composition includes an anti-inflammatory agent such as corticosteroid (including inhaled corticosteroid). The corticosteroid can be formulated for administration by inhalation. The pharmaceutical composition may be formulated with an appropriate solid or liquid carrier, depending upon the particular mode of administration chosen. Additional active ingredients include, for example, anti-infective agents (such as to prevent secondary infections), anti-inflammatory agents, bronchodilators, enzymes, expectorants, leukotriene antagonists, leukotriene formation inhibitors, and mast cell stabilizers. In addition, additional active agent include chemotherapeutics, such as for the treatment of mesothelioma.

A suitable administration format may best be determined by a medical practitioner for each subject individually. Various pharmaceutically acceptable carriers and their formulation are described in standard formulation treatises, e.g., *Remington's Pharmaceutical Sciences* by E. W. Martin. See also Wang, Y. J. and Hanson, M. A., *Journal of Parenteral Science and Technology*, Technical Report No. 10, Supp. 42: 2S, 1988.

The dosage form of the pharmaceutical composition will be determined by the mode of administration chosen. For instance, in addition to injectable fluids, inhalational and oral formulations can be employed. Inhalational preparations can include aerosols, particulates, and the like. In general, the goal for particle size for inhalation is about 1 μm or less in order that the pharmaceutical reach the alveolar region of the lung for absorption. However, the particle size can be modified to adjust the region of disposition in the lung. Thus, larger particles can be utilized (such as about 1 to about 5 μm in diameter) to achieve deposition in the repiratory bronchioles and air spaces. Oral formulations may be liquid (e.g., syrups, solutions, or suspensions), or solid (e.g., powders, pills, tablets, or capsules). For solid compositions, conventional nontoxic solid carriers can include pharmaceutical grades of mannitol, lactose, starch, or magnesium stearate. Actual methods of preparing such dosage forms are known, or will be apparent, to those of ordinary skill in the art.

The compositions or pharmaceutical compositions also can be administered by any route, including parenteral administration, for example, intravenous, intraperitoneal, intramuscular, intraperitoneal, intrasternal, or intraarticular injection or infusion, or by sublingual, oral, topical, intranasal, or transmucosal administration, or by pulmonary inhalation. When suppressive ODNs are provided as parenteral compositions, e.g. for injection or infusion, they are generally suspended in an aqueous carrier, for example, in an isotonic buffer solution at a pH of about 3.0 to about 8.0, preferably at a pH of about 3.5 to about 7.4, 3.5 to 6.0, or 3.5 to about 5.0. Useful buffers include sodium citrate-citric acid and sodium phosphate-phosphoric acid, and sodium acetate-acetic acid buffers. A form of repository or "depot" slow release preparation may be used so that therapeutically effective amounts of the preparation are delivered into the bloodstream over many hours or days following transdermal injection or delivery.

Suppressive ODNs are also suitably administered by sustained-release systems. Suitable examples of sustained-release suppressive ODNs include suitable polymeric materials (such as, for example, semi-permeable polymer matrices in the form of shaped articles, e.g., films, or mirocapsules), suitable hydrophobic materials (such as, for example, an emulsion in an acceptable oil) or ion exchange resins, and sparingly soluble derivatives (such as, for example, a sparingly soluble salt). Sustained-release suppressive ODNs may be administered orally, rectally, parenterally, intracisternally, intravaginally, intraperitoneally, topically (as by powders, ointments, gels, drops or transdermal patch), bucally, or as an oral or nasal spray.

Preparations for administration can be suitably formulated to give controlled release of suppressive ODNs. For example, the pharmaceutical compositions may be in the form of particles comprising a biodegradable polymer and/or a polysaccharide jellifying and/or bioadhesive polymer, an amphiphilic polymer, an agent modifying the interface properties of the particles and a pharmacologically active substance. These compositions exhibit certain biocompatibility features which allow a controlled release of the active substance. See U.S. Pat. No. 5,700,486.

For oral administration, the pharmaceutical compositions can take the form of, for example, tablets or capsules prepared by conventional means with pharmaceutically acceptable excipients such as binding agents (for example, pregelatinised maize starch, polyvinylpyrrolidone or hydroxypropyl methylcellulose); fillers (for example, lactose, microcrystalline cellulose or calcium hydrogen phosphate); lubricants (for example, magnesium stearate, talc or silica); disintegrants (for example, potato starch or sodium starch glycolate); or wetting agents (for example, sodium lauryl sulphate). The tablets can be coated by methods well known in the art. Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring, and sweetening agents as appropriate.

For administration by inhalation, the compounds can be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. Capsules and cartridges for use in an inhaler or insufflator can be formulated containing a powder mix of the compound and a suitable powder base such as lactose or starch.

Pharmaceutical compositions that comprise a suppressive ODN as described herein as an active ingredient will normally be formulated with an appropriate solid or liquid carrier, depending upon the particular mode of administration chosen. The pharmaceutically acceptable carriers and excipients useful in this invention are conventional. For instance, parenteral formulations usually comprise injectable fluids that are pharmaceutically and physiologically acceptable fluid vehicles such as water, physiological saline, other balanced salt solutions, aqueous dextrose, glycerol or the like. Excipients that can be included are, for instance, proteins, such as human serum albumin or plasma preparations. If desired, the pharmaceutical composition to be administered may also contain minor amounts of non-toxic auxiliary substances, such as wetting or emulsifying agents, preservatives, and pH buffering agents and the like, for example sodium acetate or sorbitan monolaurate. Actual methods of preparing such dosage forms are known, or will be apparent, to those skilled in the art.

For example, for parenteral administration, suppressive ODNs can be formulated generally by mixing them at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. A pharmaceutically acceptable carrier is a non-toxic solid, semisolid or liquid filler, diluent, encapsulating material or formulation auxiliary of any type.

Generally, the formulations are prepared by contacting the suppressive ODNs each uniformly and intimately with liquid carriers or finely divided solid carriers or both. Then, if necessary, the product is shaped into the desired formulation. Optionally, the carrier is a parenteral carrier, and in some embodiments it is a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The pharmaceutical compositions that comprise a suppressive ODN, in some embodiments, will be formulated in unit dosage form, suitable for individual administration of precise dosages. The amount of active compound(s) administered will be dependent on the subject being treated, the severity of the affliction, and the manner of administration, and is best left to the judgment of the prescribing clinician. Within these bounds, the formulation to be administered will contain a quantity of the active component(s) in amounts effective to achieve the desired effect in the subject being treated.

The therapeutically effective amount of suppressive ODN will be dependent on the ODN utilized, the subject being treated, the severity and type of the affliction, and the manner of administration. For example, a therapeutically effective amount of suppressive ODN can vary from about 0.01 μg per kilogram (kg) body weight to about 1 g per kg body weight, such as about 1 μg to about 5 mg per kg body weight, or about 5 μg to about 1 mg per kg body weight. The exact dose is readily determined by one of skill in the art based on the potency of the specific compound (such as the suppressive ODN utilized), the age, weight, sex and physiological condition of the subject.

Therapeutically effective amounts of a suppressive ODN for use in reducing occupational lung disease, such as silicosis, asbestosis or berryliosis are those that reduce inflammation, reduce the production of reactive oxygen intermediates, improve the viability of macrophages, or improve breathing or oxygenation to a desired level. As will be recognized by those in the field, an effective amount of therapeutic agent will vary with many factors including the potency of the particular ODN, the age and weight of the patient, the patient's physical condition, the oxygenation level, and other factors.

Administration may begin whenever the suppression or prevention of disease is desired, for example, at the first sign of symptoms of asbestosis, silicosis or berrylosis. Alternatively, administration may begin whenever inhalation exposure to asbestos, silica or berrylium has occurred, or prior to any possible exposure to inhaled asbestos, silica or berrylium. One administration, or multiple administrations are contemplated. For example, for an occupational exposure, daily, biweekly, weekly or monthly administrations can be effective.

C. Methods of Use

Methods are disclosed herein for treating, preventing or reducing the risk of developing occupational lung diseases, such as pneumoconiosis, including asbestosis, bronchiolitis obliterans, coal worker's pneumoconiosis, bauxite firbrosis, siderosis, byssinosis, silicosis and berryliosis. Methods are also disclosed herein for decreasing the production of reactive oxygen species in the lung, for increasing the survival of macrophages, and for decreasing the toxicity of reactive oxygen species for macrophages in the lung.

In several embodiments, the methods include administering a therapeutically effective amount of the suppressive ODN to a subject having or at risk of developing a pneumoconiosis, thereby treating or inhibiting the pneumoconiosis. In one example, the subject has or is at risk of developing silicosis. In another example, the subject has or is at risk of developing asbestosis. In a further example, the subject has or is at risk of developing berryliosis. In order to treat or prevent a pneumoconiosis and/or increase the survival of macrophages, and/or decrease the toxicity of reactive oxygen species, a therapeutically effective amount of a suppressive ODN (see above) is administered to the subject. The method can include selecting a subject exposed to, or at risk of exposure to, inorganic particles, including, but not limited to silica, asbestos, berrylium, coal dust, or bauxite. In one embodiment, the subject does not have any other medical conditions, and thus the subject has a disorder consisting of the pneumonoconiosis.

In one embodiment, the pneumoconiosis is caused by the inhalation of intermediate particles (about 1 to about 5 µm in diameter), which can penetrate to the respiratory bronchioles and air spaces. In a further embodiment, the pneumoconiosis is caused by smaller particles in the range of about 2 µm or less, such as about 1 to about 2 µm in diameter. In another embodiment, the pneumoconiosis is caused by inhalation of large particles, asbestos fibers, which are up to about 100 µm in length.

In one embodiment, the suppressive ODN can be administered locally, such as, but not limited to, administration by inhalation. Local administration of the ODN is performed by methods well known to those skilled in the art. By way of example, one method of administration to the lungs of an individual is by inhalation through the use of a nebulizer or inhaler. For example, the ODN is formulated in an aerosol or particulate and drawn into the lungs using a standard nebulizer well known to those skilled in the art.

In another embodiment, the suppressive ODN is administered systemically, such as, but not limited to, administration by injection, such as intravenous, intraperioteal or intramuscular injection.

In some examples, the suppressive ODN is administered prior to exposure to inorganic particles. In some embodiments, the ODN is administered less than three days prior to the occupational exposure. For example, the suppressive ODN can be administered about 72 hours, about 48 hours, about 36 hours, about 24 hours, about twelve hours, about eight hours, about 4 hours, about 3 hours, about 2 hours, about 1 hour, or 30 minutes or less prior to exposure to inorganic particles.

However, in some embodiments, the suppressive ODN is administered following exposure to inorganic particles. The suppressive ODNs can be administered immediately after exposure, such as within 72 hours after an exposure to the particles, such as about 72 hours, about 48 hours, about 36 hours, about 24 hours, about twelve hours, about eight hours, about 4 hours, about 3 hours, about 2 hours, about 1 hour, or 30 minutes or more after exposure to particles. In additional embodiments, the suppressive ODNs are administered following a diagnosis of pneumoconiosis, such as following a diagnosis of silicosis, asbestosis or berryliosis in a subject. Thus, the suppressive ODN can also be used to treat an existing pneumoconiosis, and thus can be administered days, months or even years after exposure. In one embodiment, a therapeutically effective amount of a suppressive ODN is administered immediately following the diagnosis of pneumoconiosis.

Combinations of these suppressive ODN are also of use. Thus, in one embodiment, more than one suppressive ODN, each with a different nucleic acids sequence, are administered to the subject. In several specific, non-limiting examples, at least two, at least three, or at least four suppressive ODNs are administered to the subject.

In another embodiment a therapeutically effective amount of an additional agent, such as an anti-inflammatory agent, bronchodilator, enzyme, expectorant, leukotriene antagonist, leukotriene formation inhibitor, or mast cell stabilizer is administered in conjunction with a suppressive ODN. In a further embodiment, a therapeutically effective amount of an anti-microbial agent is administered to the subject, such as to treat or prevent a secondary infection. The administration of the additional agent and the suppressive ODN can be sequential or simultaneous. In several examples, the additional agent is an anti-inflammatory agent, such as but not limited to cortisol, or an anti-bacterial agent.

An effective amount of a suppressive ODN can be administered in a single dose, or in multiple doses, for example daily, during a course of treatment. In one embodiment, a therapeutically effective amount of a suppressive ODN is administered as a single pulse dose, as a bolus dose, or as pulse doses administered over time. Thus, in pulse doses, a bolus administration of a suppressive ODN is provided, followed by a time period wherein no suppressive ODN is administered to the subject, followed by a second bolus administration. In specific, non-limiting examples, pulse doses of a suppressive ODN are administered during the course of a day, during the course of a week, or during the course of a month. The administration of the ODN can be regulated to correspond with the timing of an occupational exposure.

The effectiveness of treatment with a suppressive ODN can be measured by monitoring pulmonary function by methods known to those of skill in the art. For example, various measurable parameters of lung function can be studied before, during, or after treatment. Pulmonary function can be monitored by testing any of several physically measurable operations of a lung including, but not limited to, inspiratory flow rate, expiratory flow rate, and lung volume. A statistically significant increase, as determined by mathematical formulas well known to those skilled in the art, in one or more of these parameters indicates efficacy of the suppressive ODN treatment.

The methods of measuring pulmonary function most commonly employed in clinical practice involve timed measurement of inspiratory and expiratory maneuvers to measure specific parameters. For example, FVC measures the total volume in liters exhaled by a patient forcefully from a deep initial inspiration. This parameter, when evaluated in conjunction with the FEV1, allows bronchoconstriction to be quantitatively evaluated. A statistically significant increase, as determined by mathematical formulas well known to those skilled in the art, in FVC or FEV1 reflects a decrease in bronchoconstriction, and indicates that suppressive ODN therapy is effective.

A problem with forced vital capacity determination is that the forced vital capacity maneuver (i.e., forced exhalation from maximum inspiration to maximum expiration) is largely technique dependent. In other words, a given subject may produce different FVC values during a sequence of consecutive FVC maneuvers. The FEF 25-75 or forced expiratory flow determined over the midportion of a forced exhalation maneuver tends to be less technique dependent than the FVC. Similarly, the FEV1 tends to be less technique-dependent than FVC. Thus, a statistically significant increase, as determined by mathematical formulas well known to those skilled in the art, in the FEF 25-75 or FEV1 reflects a decrease in bronchoconstriction, and indicates that suppressive ODN therapy is effective.

In addition to measuring volumes of exhaled air as indices of pulmonary function, the flow in liters per minute measured over differing portions of the expiratory cycle can be useful in determining the status of a patient's pulmonary function. In particular, the peak expiratory flow, taken as the highest airflow rate in liters per minute during a forced maximal exhalation, is well correlated with overall pulmonary function in a patient with asthma and other respiratory diseases. Thus, a statistically significant increase, as determined by mathematical formulas well known to those skilled in the art, in the peak expiratory flow following administration of a suppressive ODN indicates that the therapy is effective.

The effectiveness of treatment with a suppressive ODN can be detected by other indicators. In other embodiments, decreased infection, decreased development of tumors, decreased coughing and other symptoms, can indicate that the treatment is effect.

Methods are also disclosed for increasing the viability of macrophages exposed to an inorganic particle. The methods include contacting the macrophages with an effective amount of a suppressive ODN, as described above. The macrophage can be in vivo or in vitro.

In one embodiment, the macrophages are in vivo. Thus, the methods can also include assaying for the viability of macrophages in a sample from the subject, such as, but not limited to bronchoalveolar lavage fluid, a sputum sample, a biopsy sample, a blood sample, or any sample that includes white blood cells. The method can include assaying the number of macrophages in a sample.

The methods can also include assaying for the presence of reactive oxygen species (ROS) in a sample. The sample can be a biological sample from a subject, such as sputum, serum, blood, biopsy or bronchoaleolar lavage fluid sample. However, the sample can also be a sample of a macrophage or a cell line cultured in vitro. Generally, a decrease in the amount of reactive oxygen species, or an increase in the number of macrophages, as compared to a control, indicates that treatment with a suppressive ODN is effective.

Suitable controls include, but are not limited to, a sample from the same subject prior to treatment with the suppressive ODN, but after exposure to the inorganic particles, a sample from another subject exposed to inorganic particles by not treated with suppressive ODN, or a control (standard) value, or a sample macrophages exposed to particles in vitro but not treated with the suppressive ODN. Exemplary methods for detecting ROS are described below.

Disclosed herein are methods of decreasing the toxicity associated with reactive oxygen intermediates in the lung. The methods include treating a subject with a suppressive oligodeoxynucleotide as described above, obtaining a sample from the subject, and measuring the generation of reactive oxygen intermediates. For example, the sample can be a bronchiolar lavage sample, a lung biopsy sample, or a sputum sample. The methods can include measuring the generation of hydrogen peroxide or superoxide. The methods can also include measuring p47phox expression. For example, p47phox mRNA can be measured, using such techniques as qualitative or quantitative reverse transcriptase (RT)-polymerase chain reaction (PCR), Northern blot or dot blot. In other examples, p47phox protein can be measured, using techniques such as an immunoassay, including a radio-immunoassay or an enzyme linked immunosorbant assay (ELISA), or Western blot.

In embodiment, the generation of ROS is measured in a sample, such as a biological sample, such as a sample including macrophages using cytochrome c reduction. In one non-limiting example, NADPH or NADH is used as the reducing substrate, in a concentration of about 100 µM. The reduction of cytochrome c is monitored spectrophotometrically by the increase in absorbance at 550 nm, assuming an extinction coefficient of 21 mM$^{-1}$ cm$^{-1}$. The assay is performed in the absence and presence of about 10 µg superoxide dismutase. The superoxide-dependent reduction is defined as cytochrome c reduction in the absence of superoxide dismutase minus that in the presence of superoxide dismutase (Uhlinger et al., J. Biol. Chem. 266, 20990-20997, 1997). Acetylated cytochrome c may also be used, since the reduction of acetylated cytochrome c is thought to be exclusively via superoxide.

In another embodiment, the generation of ROS is measured in a sample, such as a biological sample, using nitroblue tetrazolium (NBT) reduction. In another example, the same general protocol is used, except that NBT is used in place of cytochrome c. In general, about 1 mL of filtered 0.25% nitrotetrazolium blue (Sigma, St. Louis, Mo.) is added in Hanks buffer without or with about 600 Units of superoxide dismutase (Sigma) and samples are incubated at approximately 37° C. The oxidized NBT is clear, while the reduced NBT is blue and insoluble. The insoluble product is collected by centrifugation, and the pellet is re-suspended in about 1 mL of pyridine (Sigma) and heated for about 10 minutes at 100° C. to solubilize the reduced NBT. The concentration of reduced NBT is determined by measuring the absorbance at 510 nm, using an extinction coefficient of 11,000 M$^{-1}$cm$^{-1}$. Untreated wells are used to determine cell number.

In a further embodiment, superoxide generation can be monitored with a chemiluminescence detection system utilizing lucigenin (bis-N-methylacridinium nitrate, Sigma, St. Louis, Mo.). The sample is mixed with about 100 µM NADPH (Sigma, St. Louis, Mo.) and 10 µM lucigenin (Sigma, St. Louis, Mo.) in a volume of about 150 µL Hanks solution. Luminescence is monitored in a 96-well plate using a LumiCounter (Packard, Downers Grove, Ill.) for 0.5 second per reading at approximately 1 minute intervals for a total of about 5 minutes; the highest stable value in each data set is used for comparisons. As above, superoxide dismutase is added to some samples to prove that the luminescence arises from superoxide. A buffer blank is subtracted from each reading (Ushio-Fukai et al., J. Biol. Chem. 271, 23317-23321, 1996).

Cytokine levels in body fluids or cell samples are determined by conventional methods known by those of skill in the art. For example, cytokine concentrations in cell culture supernatants and BAL fluid can be measured as recommended by the manufacturer of ELISA kits (R&D systems, Minneapolis, Minn.). Cytotoxicity can be measured using any assay known to one of skill in the art. Exemplary assays include the use of $^3$H-thymidine, a 3-(4,5-dimethylthiazol-2-yl)-2,5,diephenyltetraolium bromide (MTT) assay, and an lactose dehydrogenase (LDH) assay.

The disclosure is illustrated by the following non-limiting Examples.

EXAMPLES

It is disclosed herein that a pneumonconiosis can be treated by the administration of suppressive ODN. One form of occupational lung disease is silicosis. Inhalation of silica-containing dust particles induces silicosis, an inflammatory disease of the lungs characterized by the infiltration of macrophages and neutrophils into the lungs and the production of pro-inflammatory cytokines, chemokines, and reactive oxygen species (ROS). The potential of suppressive ODN to prevent acute murine silicosis was examined. As disclosed below, in vitro studies indicate that suppressive ODN blunt silica-induced macrophage toxicity. This effect was associated with a reduction in ROS production and p47phox expression (a sub-unit of NADPH oxidase key to ROS generation). In vivo studies show that pre-treatment with suppressive (but not control) ODN reduces silica dependent pulmonary inflammation, as manifest by fewer infiltrating cells, less cytokine/chemokine production, and lower levels of ROS (p<0.01 for all parameters). Treatment with suppressive ODN also reduced disease severity and improved the survival (p<0.05) of mice exposed to silica. These studies demonstrate that immunosuppressive ODN can be used to treat pneumoconiosis, including silicosis, asbestosis and berylliosis.

Example 1

Materials and Methods

Oligodeoxynucleotides and Reagents: Phosphorothioate oligodeoxynucletoides (ODNs) were synthesized at the Center for Biologics Evaluation and Research core facility (Bethesda, Md.). The following exemplary ODNs were used in the studies described below: suppressive ODN; TTAGGGTTAGGGTTAGGGTTAGGG (SEQ ID NO: 2), control ODN; TTCAAATTCAAATTCAAATTCAAA (SEQ ID NO: 26). ODN contained <0.1 units of endotoxin/mg, as assessed by a Limulus amebocyte cell lysate assay. Silica particles were obtained from U.S. Silica (Berkeley Springs, W. Va.) and were sterilized at 200° C. for 2 hours (hr) to inactivate any contaminating endotoxin (Arras et al., *Am. J. Respir. Cell Mol. Biol.* 24:368-375, 2001).

In vitro studies: The mouse macrophage-like cell line RAW264.7 and the murine bronchial cell line MM14.Lu were purchased from American Type Cell Culture (Manassas, Va.) and maintained in RPMI 1640 medium supplemented with 10% FCS, 100 U/ml penicillin, 100 g/ml streptomycin, 25 mM HEPES, 1.0 mM sodium pyruvate, nonessential amino acids and 0.0035% 2-mercaptoethanol. Peritoneal cells were isolated from mice injected i.p. with 3% thioglycolate, as previously described (Shirota et al., *J. Immunol.* 174:4579-4583, 2005). Single cells suspensions were allowed to attach to the plate over 24 hours and were then cultured with 20-40 g/cm$^2$ of silica in 6- or 96-well plates. Phosphorotioate ODNs were added to culture 1 hour before the introduction of silica.

In vivo Studies: Ten-week-old female BALB/c mice were obtained from the National Cancer Institute (Frederick, Md.). Mice were anesthesized using a mixture of ketamine (80 mg/kg) and xylazine (10 mg/kg). Silicosis was induced by the intra-tracheal instillation of 2.5 mg of sterilized silica particles (MIN-U-SIL 5; mean particle size 1.7 m) in 100 l of sterile saline as previously described (26). Some mice were treated by i.p. injection of 300 g of suppressive or control ODN 24 and 3 hours prior to silica administration. Bronchoalveolar lavage (BAL) fluid was collected from anesthetized mice by delivering and then removing 0.8 ml of PBS into the lungs 5 times, using a 22-gauge catheter (Faffe et al., *J. Appl. Physiol* 90:1400-1406, 2001). Cell differentials (200 cells counted) were performed on cytocentrifuge preparations of BAL after methanol fixation and staining with Diff-Quick (Dade Behring, Newark, Del.).

Cytokine ELISA: Cytokine levels in BAL and culture supernatants were measured by ELISA, as previously described (Klinman et al., *Proc. Natl. Acad. Sci. USA* 93:2879-2883, 1996). Paired IL-6 and IL-12-specific monoclonal antibodies (mAbs) were purchased from BD Pharmingen (San Diego, Calif.), and KC-specific mAb from R&D Systems (Minneapolis, Minn.). Ninety-six-well Immulon H2B plates (Thermo LabSystems) were coated with capture cytokine-specific Abs and then blocked with PBS/1% bovine serum albumin (BSA). BAL or culture supernatants were added, and bounded cytokines detected by the addition of biotin-labeled secondary antibody (Ab), followed by phosphatase-conjugated avidin and a phosphatase-specific colorimetric substrate. Standard curves were generated using recombinant cytokines purchased from R&D Systems.

Cell Viability Assays: Silica-mediated cytotoxicity was assessed using both MTT [3-(4,5-dimethylthiazol-2-yl)-2,5-diphenyltetrazolium bromide] and LDH (lactase dehydrogenase) assays. Cells were seeded in 96-well plates at a density of 10,000 cells/well and allowed to adhere for 24 hours. The cultures were then exposed to silica particles±3 µM of suppressive or control ODN for 24 hr. Culture supernatants were collected and analyzed using an LDH release kit (Roche Applied Sciences, Indianapolis, Ind.). Briefly, the kit's catalyst and dye solution were mixed and added to the culture supernatants for 30 minutes at room temperature. The reaction was stopped, and LDH concentration quantified colorimetrically by comparison to a standard curve.

An MTT assay was performed on cells that had been cultured with silica±ODN as described above. Briefly, 100 µl of media containing MTT (Sigma; 0.5 mg/ml) was added to the adherent cells for 2 hr. Non-internalized MTT was then washed away, and the cells lysed by the addition of 50 µl DMSO. This released the MTT internalized by viable cells. MTT concentration was measured colorimetrically, and cell viability determined as the optical density at 570 nm of treated/untreated cultures.

Detection of Reactive Oxygen Species (ROS): 100,000 cells were cultured with 40 g/cm$^2$ of silica particles±3 M of ODN in 96-well plates for 24 hours in medium lacking phenol red (which interferes with the hydrogen peroxide colorimetric assay). Culture media was collected after 24 hours and $H_2O_2$ levels quantified using an $Fe^{3+}$-xylenol orange reaction kit (BioAssay Systems; Heyward, Calif.) as recommended by the manufacturer. Duplicate assays in which supernatants were treated for 5' with 0.5 U/well of murine liver-derived catalase (Sigma) were run to insure that the activity measured reflected $H_2O_2$ concentration.

Western Blots: Cells were cultured with 40 µg/cm2 of silica particles±3 M of ODN for 24 hr, and then lysed in cold buffer containing 137 mM sodium chloride, 20 mM Tris, 1 mM EDTA, 50 mM sodium fluoride, 1% Triton X, and protease inhibitor. Protein concentrations were determined using a BCA Protein Assay Kit (Pierce, Rockford, Ill.), and 10 µg of whole cell extract then boiled for 5 minutes in sample buffer. The boiled samples were run on 4-12% gradient SDS-PAGE, and transferred onto a PVDF membrane Immunoblots were probed with Ab specific to p47phox (Upstate, Lake Placid, N.Y.), followed by HRP-conjugated secondary Ab (Amersham, Buck, UK). Signals were visualized by enhanced chemiluminescence system using an ECL kit (Amersham). Blots were re-probed with anti-actin Ab (Sigma-Aldrich, St. Louis, Mo.) to normalize for protein loading.

Statistical Analysis: Statistical analyses were performed using MedCalc, version 9.3.7.0 (MedCalc Softwere, Mariakerke, Belgium) and S-Plus (Version 7, Insightful Corp). Differences between groups were assessed using a one-way analysis of variance (ANOVA) with Bonferroni post-hoc test control for type I error. Differences in survival were determined using the log rank test of Kaplan-Meier. Analysis of weight loss was performed using mixed effects longitudinal regression models (Pinheiro and Bates, *Mixed Effects Models in S and S-Plus*. Springer-Verlag, New York, N.Y., 2000). All tests were two-sided; probability values less than 0.05 were considered significant. All values are expressed as means±SE unless otherwise noted.

Example 2

Suppressive ODN Reduce the Inflammatory Response of MM14.Lu Lung Cells Cultured with Silica The murine MM14.Lu cell line provides a in vitro model for studying the effect of silica exposure on pulmonary cells. MM14.Lu cells incubated with 40 μg/cm$^2$ of silica respond by producing the pro-inflammatory chemokine KC (FIG. 1). The inclusion of suppressive ODN during culture abrogated this silica-induced KC production in a dose-dependent manner ($p<0.01$), whereas control ODN had no effect (FIG. 1). Of note, a similar down-regulation in IL-6 production by silica-stimulated MM14.Lu cells treated with suppressive ODN was also observed.

Example 3

Suppressive ODN Reduce the Production of Reactive Oxygen Species (ROS) and Improve the Viability of Macrophages Cultured with Silica Macrophages contribute to the lung pathology induced by silica inhalation (3). Macrophages exposed to silica produce ROS (including $H_2O2$) via a p47phox dependent pathway (Rimal et al., *Curr. Opin. Pulm. Med.* 11:169-173, 2005; Sayes et al., *Toxicol. Sci.* 97:163-180, 2007; Persson, *Toxicol. Lett.* 159:124-133, 2005; Giorgio et al., *Nat. Rev. Mol. Cell Biol.* 8:722-728, 2007; Bedard and Krause., *Physiol Rev.* 87:245-313, 2007; Teissier et al., *Circ. Res.* 95:1174-1182, 2004; Von and Brune, *J. Immunol.* 169:2619-2626, 2002; Gercken et al., *Toxicol. Lett.* 88:121-129, 1996; Shen et al., *Am. J. Physiol Lung Cell Mol. Physiol* 280:L10-L17-L17, 2001; Becher et al., *Inhal. Toxicol.* 19:645-655, 2007). Consistent with those findings, peritoneal macrophages and the RAW264.7 macrophage cell line exposed to silica particles in vitro responded by up-regulating p47phox expression and producing large amounts of $H_2O_2$ (FIGS. 2, 3, $p<0.05$). The elevation in both $H_2O_2$ secretion and p47phox expression were significantly blunted by treatment with suppressive (but not control) ODN ($p<0.05$).

Silica exposure can also result in macrophage death. The viability of RAW264.7 cells and freshly isolated peritoneal macrophages was monitored by both MTT and LDH release assays. As expected, macrophage viability was significantly reduced by culture with 10-40 μg/cm2 of silica for 24 hours (FIG. 4). Treating the silica-exposed macrophages with suppressive (but not control) ODN significantly improved their viability, consistent with suppressive ODN preventing silica-dependent inflammatory damage (FIG. 4, $p<0.05$).

Example 4

Suppressive ODN Inhibit Silica-Induced Pulmonary Inflammation in Vivo

The ability of suppressive ODN to prevent pulmonary inflammation was examined in a murine model of acute silicosis. As previously described, silicosis was induced by instilling 2.5 mg of silica via an intra-tracheal catheter into the lungs of normal BALB/c mice. The resultant inflammatory response peaked three days later, and was characterized by a pulmonary infiltrate dominated by neutrophils and the production of inflammatory cytokines and chemokines. To assess whether treatment with suppressive ODN reduced this inflammation, two doses of suppressive ODN were administered one day prior to silica installation.

Bronchoalveolar lavage fluid (BAL) was collected from mice on days 1, 3, 5, 7 and 14. As seen in FIG. 5A, silica instillation resulted in a significant increase in BAL cellularity by day 3 (rising from $1.3 \times 10^5$ cells/ml in controls to $14.6 \times 10^5$ cells/ml in mice treated with silica; $p<0.01$). This pulmonary infiltrate consisted primarily of neutrophils (79.4±4.9%) with some macrophages (20.2±4.6%), whereas BAL from normal mice was composed almost exclusively of macrophages (96.0±1.0%; FIGS. 5A, 5B). Among mice pre-treated with suppressive ODN, the silica-induced increase in BAL cellularity and associated neutrophil accumulation were significantly reduced at peak, and resolved more rapidly ($p<0.01$; FIG. 5B, FIG. 5C). No such beneficial effects were observed when mice were pre-treated with control ODN, establishing the specificity of these outcomes.

Consistent with previous studies (Huax et al., *Am. J. Respir. Cell Mol. Biol.* 20:561-572, 1999; Yuen et al., *Am. J. Respir. Cell Mol. Biol.* 15:268-274, 1996), silica instillation also triggered a significant increase in the level of KC in BAL ($p<0.01$, FIG. 6). The production of this inflammatory chemokine was reduced by nearly 50% in mice pre-treated with suppressive (but not control) ODN (FIG. 6, $p<0.01$). The silica-induced production of pulmonary IL-12 was similarly reduced by suppressive ODN treatment.

It was difficult to detect $H_2O_2$ in BAL (which is diluted upon collection), but consistent with the ability of silica to trigger ROS production by macrophages in vitro, $H_2O_2$ levels were significantly elevated in the serum of mice 3 days post silica instillation (FIG. 7, $p<0.01$). Treating these mice with suppressive ODN resulted in a significant reduction in systemic $H_2O_2$ levels (FIG. 7, $p<0.01$).

Example 5

Suppressive ODN Reduce the Pathology Induced by in Vivo Silica Exposure

The inflammatory response induced by instilling silica into the lungs of normal BALB/c mice had a systemic impact on animal health, as evidenced by significant weight loss (>12%) that peaked on day 3 and persisted for greater than 2 weeks (FIG. 8). Both the magnitude and duration of this weight loss were significantly reduced among mice pre-treated with suppressive ODN (FIG. 8, $p<0.0008$, mixed effects longitudinal regression analysis). This effect was sequence specific, as control ODN had no significant effect on silica-induced weight loss ($p=0.37$).

The pulmonary inflammation induced by silica instillation caused appreciable mortality. Approximately 25% of the mice treated with silica alone and 40% of the animals treated with silica plus control ODN died by day 7 (FIG. 9). Histologic analysis of BAL from these animals showed massive inflammatory cell infiltration and alveolar hemorrhage, both of which are consistent with acute silicosis as the cause of death. Of note, the modest (albeit not statistically significant) effect of control ODN on weight loss was primarily attributable to the death of severely ill animals. Consistent with the beneficial impact of suppressive ODN on silica-induced pathology, there were no deaths among the silica-instilled mice treated with suppressive ODN ($p<0.05$).

Exposure to silica-containing dust can lead to acute and chronic pulmonary diseases including silicosis and lung cancer (Ding et al., *Int. Immunopharmacol.* 2:173-182, 2002). Evidence suggests that silica-dependent lung damage is mediated by the production of reactive oxygen species by macrophages in situ (Fubini and Hubbard, supra, 2003; Klaunig and Kamendulis. *Annu. Rev. Pharmacol. Toxicol.*

44:239-267, 2004, Kinnula, *Am. J. Respir. Crit Care Med.* 172:417-422, 2005). It is disclosed herein that suppressive ODN block the production of ROS by silica-activated macrophages, and reduce the pulmonary damage characteristic of acute silicosis.

Macrophages are the predominant immune cell present in alveoli and are rapidly activated by silica particles in situ (neutrophil infiltration is a subsequent event) (Fubini and Hubbard, supra, 2003; van der Van et al., *Toxicol. Appl. Pharmacol.* 168:131-139, 200; Gossart et al., *J. Immunol.* 156: 1540-1548, 1996). Crystalline silica triggers a respiratory burst in phagocytes characterized by the early production of superoxide (O2-), followed by $H_2O_2$ release via phagocytic oxidase (phox), NADPH oxidase (NOX), and mitochondrial oxidase production, all of which contribute to cell death (Fubini and Hubbard, supra, 2003; Giorgio, supra, 2007; Sarih, *J. Leukoc. Biol.* 54:407-413, 2002). This study examined the effect of suppressive ODN on RAW264.7 cells and freshly isolated murine macrophages exposed to silica. Consistent with previous reports, macrophages cultured with silica produced large amounts of $H_2O_2$ (FIG. 2). It was also established that exogenously administered $H_2O_2$ significantly reduced the viability of RAW264.7 cells. The studies presented herein show that macrophages treated with suppressive ODN are protected from $H_2O_2$ and silica-induced toxicity in vitro (FIG. 2), while mice treated with suppressive ODN are resistant to the mortality and morbidity mediated by silica instillation (FIGS. 8 and 9).

ROS are directly toxic to lung cells. By promoting the production of inflammatory cytokines and chemokines via the NF-B pathway, ROS also facilitate the infiltration of neutrophils into the lungs (Sato et al., *Am. J. Respir. Crit Care Med.* 174:906-914, 2006; Gossart et al., *J. Immunol.* 156: 1540-1548, 1996; Barrett et al., *Am. J. Physiol* 276:L979-L988-L988, 1999; Stringer et al., *J. Toxicol. Environ. Health A* 55:31-44, 1998; Lugano et al., *Am. J. Pathol.* 109:27-36, 1982; Hu et al., *J. Toxicol. Environ. Health A* 70:1403-1415, 2007). p47phox (Persson et al., *Toxicol. Lett.* 159:124-133, 2005) and mitochondrial pathway (Hu et al., supra, 2007) play a critical role in mediating silica-induced ROS production (Von et al., *J. Immunol.* 169:2619-2626, 2002; Liu et al., *Free Radic. Biol. Med.* 42:852-863, 2007). Since suppressive ODN maintained mitochondrial viability assessed by MTT and LDH in non-phagocytized macrophage cells, RAW 264.7 (FIG. 4), silica-induced ROS could be derived mainly by p47phox.

The results show that suppressive ODN inhibit this activity thereby attenuating $H_2O_2$ generation (FIGS. 2, 3 and 7). As a consequence, suppressive ODN significantly reduce both the cellular toxicity and pulmonary inflammation induced by silica exposure, improving survival and reducing morbidity in silica-challenged mice (FIGS. 8, 9).

Hydrogen peroxide was used as a marker for ROS generation since i) silica-activated macrophages produce large amounts of $H_2O_2$ via the ROS pathway and ii) $H_2O_2$ levels correlate with intracellular oxidative stress and tissue pathology in acute silicosis (Fubini and Hubbard, *Free Radic. Biol. Med.* 34:1507-1516, 2003; Giorgio et al., supra, 2007; Liu et al., *Am. J. Respir. Cell Mol. Biol.* 36:594-599, 2007). The effect of suppressive ODN on cytokine and chemokine production were also examined. As expected, suppressive ODN inhibited the silica-induced production of IL-6, IL-12 and KC in vitro and in the lungs (FIGS. 1 and 6). These effects were dose dependent and sequence specific (as control ODN had no effect).

Studies were conducted to identify an initial treatment regimen that optimized the effectiveness of suppressive ODN in acute murine silicosis. Those studies established that a single dose of suppressive ODN reduced lung inflammation, weight loss and improved the survival of mice challenged intra-tracheally with 0.25-2.5 mg of silica; two doses of suppressive ODN were more effective. In addition, optimal protection was observed when suppressive ODN were delivered shortly before exposure to the inflammatory stimulus (consistent with studies in which suppressive ODN mediated protection against toxic shock) (Shirota et al., supra, 2005).

Example 6

Suppressive ODN Inhibit Asbestos-Induced Pulmonary Inflammation in Vivo

The ability of suppressive ODN to prevent pulmonary inflammation was examined in a murine model of asbestosis. ELISA assays were used to determine the concentration of KC and IL12 in BAL fluid.

Ten-week-old female BALB/c mice were anesthesized using a mixture of ketamine (80 mg/kg) and xylazine (10 mg/kg). Asbestosis was induced by the intra-tracheal instillation of delivery of 0.14 mg crocidolite asbestos. Mice treated by i.p. injection of 300 g of suppressive or control ODN or saline 24 and 3 hours prior to asbestos administration. The following suppressive ODN was used:

suppressive ODN: TTAGGGTTAGGGTTAGGGTTAGGG (SEQ ID NO: 2). The control ODN was ODN1612 (GCTAGAGCTTAGGCT, SEQ ID NO: 27).

Bronchoalveolar lavage (BAL) fluid was collected from anesthetized mice as described above, by delivering and then removing 0.8 ml of PBS into the lungs 5 times, using a 22-gauge catheter (Faffe et al., *J. Appl. Physiol* 90:1400-1406, 2001) at 1 and 7 days. Cytokine levels in BAL were measured by ELISA, as previously described (Klinman et al., *Proc. Natl. Acad. Sci. USA* 93:2879-2883, 1996). Paired keratinocyte chemoattractant (KC) and IL-12-specific monoclonal antibodies (mAbs) were utilized. As described above, ninety-six-well Immulon H2B plates (Thermo LabSystems) were coated with capture cytokine-specific Abs and then blocked with PBS/1% bovine serum albumin (BSA). BAL were added, and bounded cytokines detected by the addition of labeled second antibody. Standard curves were generated using recombinant cytokines, as described above. Three independent experiments were conducted using a combined total of 9-14 mice per group. The data was analyzed by a Student's T test to determine statistical significance. The following result were obtained:

|  | IL-12 level 1 Day | IL-12 level 7 Days | KC level 1 Day | Level 7 Days |
|---|---|---|---|---|
| Asbestos alone | 18.1 + 6.5 | 33.7 + 17.8 | 35.01 + 23.74 | 24.99 + 19.43 |
| Asbestos + Control ODN | 13.8 + 7.8 | 27.2 + 21.8 | 43.86 + 59.73 | 22.93 + 17.06 |
| Asbestos + Sup ODN | 7.8 + 4.9 | 12.3 + 6.2 | 16.62 + 19.13 | 9.45 + 5.56 |

Statistical analyses were performed. The p values are shown below:

| | | | | |
|---|---|---|---|---|
| Asbestos versus control | 0.11 | 0.28 | 0.59 | 0.80 |
| Asbestos versus Sup ODN | 0.001 | 0.003 | 0.04 | 0.03 |
| Control ODN versus Sup ODN | 0.04 | 0.04 | 0.12 | 0.03 |

These results demonstrate an effect of sup ODN on IL-2 and KC production in asbestos induced inflammation. Specifically, treatment with suppressive ODNs resulted in a statistically significant decrease in the production of both IL-1 and KC.

It will be apparent that the precise details of the methods or compositions described may be varied or modified without departing from the spirit of the described invention. We claim all such modifications and variations that fall within the scope and spirit of the claims below.

The invention claimed is:

1. A method of inhibiting silicosis or asbestosis in a subject comprising
selecting a subject having silicosis or asbestosis, or at risk of developing silicosis or asbestosis due to an exposure to silica or asbestos, respectively; and
administering parenterally to the subject having silicosis or asbestosis or at risk of developing silicosis or asbestosis an amount of a suppressive oligodeoxynucleotide effective to inhibit pulmonary inflammation induced by particle inhalation, wherein the suppressive oligodeoxynucleotide comprises the nucleic acid sequence set forth as SEQ ID NO: 2 and is at most 40 nucleotides in length, thereby inhibiting silicosis or asbestosis in the subject.

2. The method of claim 1, wherein the subject has silicosis.

3. The method of claim 1, wherein the subject is at risk of having asbestosis.

4. The method of claim 1, wherein the suppressive oligodeoxynucleotide is administered to an individual at risk of silicosis or asbestosis due to an occupational exposure to inorganic particles.

5. The method of claim 1, wherein the composition is administered to an individual who has inhaled silica or asbestos particles due to an occupational exposure.

6. The method of claim 1, wherein the composition is administered systemically to the individual.

7. The method of claim 1, further comprising administering to the subject a therapeutically effective amount of an anti-infective agent, an anti-inflammatory agent, a bronchodilator, an expectorant, a leukotriene antagonist, or a mast cell stabilizer.

8. The method of claim 1, further comprising detecting the generation of reactive oxygen intermediates in a sample from the subject.

9. The method of claim 1, further comprising detecting the presence of macrophages in a sample from the subject.

10. A method for treating silicosis or asbestosis in a subject, comprising
selecting a subject exposed to silica particles or exposed to asbestosis particles; and
administering parenterally to the subject a therapeutically effective amount of an oligodeoxynucleotide comprising the nucleic acid sequence set forth as SEQ ID NO: 2, wherein the oligodeoxynucleotide is at most 30 nucleotides in length, thereby treating silicosis or asbestosis in the subject.

11. A method for reducing the risk of developing silicosis or asbestosis in a subject, comprising
selecting a subject at risk of exposure to silica particles or asbestos particles; and
administering parenterally to the subject a therapeutically effective amount of an oligodeoxynucleotide comprising the nucleic acid sequence set forth as SEQ ID NO: 2, wherein the oligodeoxynucleotide is at most 30 nucleotides in length, thereby reducing the subject's risk of developing silicosis or asbestosis.

12. The method of claim 10, wherein the method is a method for treating asbestosis, and wherein the method comprises selecting a subject exposed to asbestos particles.

13. The method of claim 10, wherein the method is a method for treating silicosis, and wherein the method comprises selecting a subject exposed to silica particles.

14. The method of claim 11, comprising selecting a subject at risk of exposure to silica particles, and administering to the subject a therapeutically effective amount of an oligodeoxynucleotide comprising the nucleic acid sequence set forth as SEQ ID NO: 2, wherein the oligodeoxynucleotide is at most 30 nucleotides in length, thereby reducing the subject's risk of developing silicosis.

15. The method of claim 1, wherein the oligodeoxynucleotide consists of the nucleic acid sequence set forth as SEQ ID NO: 2.

16. The method of claim 14, wherein the oligodeoxynucleotide consists of the nucleic acid sequence set forth as SEQ ID NO: 2.

* * * * *

SEQUENCE LISTING

```
<160> NUMBER OF SEQ ID NOS: 28

<210> SEQ ID NO 1
<211> LENGTH: 24
<212> TYPE: DNA
<213> ORGANISM: Artificial sequence
<220> FEATURE:
<223> OTHER INFORMATION: Synthetic  oligodeoxynucleotide (ODN)

<400> SEQUENCE: 1
ttagggttag ggttagggtt aggg                                             24

<210> SEQ ID NO 2
<211> LENGTH: 18
<212> TYPE: DNA
<213> ORGANISM: Artificial sequence
<220> FEATURE:
<223> OTHER INFORMATION: Synthetic  oligodeoxynucleotide (ODN)

<400> SEQUENCE: 2
ttagggttag ggttaggg                                                    18

<210> SEQ ID NO 3
<211> LENGTH: 12
<212> TYPE: DNA
<213> ORGANISM: Artificial sequence
<220> FEATURE:
<223> OTHER INFORMATION: Synthetic  oligodeoxynucleotide (ODN)

<400> SEQUENCE: 3
ttagggttag gg                                                          12

<210> SEQ ID NO 4
<211> LENGTH: 24
<212> TYPE: DNA
<213> ORGANISM: Artificial sequence
<220> FEATURE:
<223> OTHER INFORMATION: Synthetic  oligodeoxynucleotide (ODN)

<400> SEQUENCE: 4
tgggcggttg ggcggttggg cggt                                             24

<210> SEQ ID NO 5
<211> LENGTH: 16
<212> TYPE: DNA
<213> ORGANISM: Artificial sequence
<220> FEATURE:
<223> OTHER INFORMATION: Synthetic  oligodeoxynucleotide (ODN)

<400> SEQUENCE: 5
tgggcggttg ggcggt                                                      16
```

```
<210> SEQ ID NO 6
<211> LENGTH: 16
<212> TYPE: DNA
<213> ORGANISM: Artificial sequence
<220> FEATURE:
<223> OTHER INFORMATION: Synthetic  oligodeoxynucleotide (ODN)

<400> SEQUENCE: 6
tcaaccttca ttaggg                                                    16

<210> SEQ ID NO 7
<211> LENGTH: 22
<212> TYPE: DNA
<213> ORGANISM: Artificial sequence
<220> FEATURE:
<223> OTHER INFORMATION: Synthetic  oligodeoxynucleotide (ODN)

<400> SEQUENCE: 7
ttagggttag ggtcaacctt ca                                             22

<210> SEQ ID NO 8
<211> LENGTH: 22
<212> TYPE: DNA
<213> ORGANISM: Artificial sequence
<220> FEATURE:
<223> OTHER INFORMATION: Synthetic  oligodeoxynucleotide (ODN)

<400> SEQUENCE: 8
tcaaccttca ttagggttag gg                                             22

<210> SEQ ID NO 9
<211> LENGTH: 22
<212> TYPE: DNA
<213> ORGANISM: Artificial sequence
<220> FEATURE:
<223> OTHER INFORMATION: Synthetic  oligodeoxynucleotide (ODN)

<400> SEQUENCE: 9
gggttagggt tatcaacctt ca                                             22

<210> SEQ ID NO 10
<211> LENGTH: 22
<212> TYPE: DNA
<213> ORGANISM: Artificial sequence
<220> FEATURE:
<223> OTHER INFORMATION: Synthetic  oligodeoxynucleotide (ODN)

<400> SEQUENCE: 10
tcaaccttca gggttagggt ta                                             22

<210> SEQ ID NO 11
<211> LENGTH: 22
<212> TYPE: DNA
<213> ORGANISM: Artificial sequence
<220> FEATURE:
<223> OTHER INFORMATION: Synthetic  oligodeoxynucleotide (ODN)

<400> SEQUENCE: 11
gggtgggtgg gtattaccat ta                                             22

<210> SEQ ID NO 12
<211> LENGTH: 22
<212> TYPE: DNA
<213> ORGANISM: Artificial sequence
<220> FEATURE:
```

<223> OTHER INFORMATION: Synthetic oligodeoxynucleotide (ODN)

<400> SEQUENCE: 12
attaccatta gggtgggtgg gt    22

<210> SEQ ID NO 13
<211> LENGTH: 18
<212> TYPE: DNA
<213> ORGANISM: Artificial sequence
<220> FEATURE:
<223> OTHER INFORMATION: Synthetic oligodeoxynucleotide (ODN)

<400> SEQUENCE: 13
tgggcggttc aagcttga    18

<210> SEQ ID NO 14
<211> LENGTH: 18
<212> TYPE: DNA
<213> ORGANISM: Artificial sequence
<220> FEATURE:
<223> OTHER INFORMATION: Synthetic oligodeoxynucleotide (ODN)

<400> SEQUENCE: 14
tcaagcttca tgggcggt    18

<210> SEQ ID NO 15
<211> LENGTH: 22
<212> TYPE: DNA
<213> ORGANISM: Artificial sequence
<220> FEATURE:
<223> OTHER INFORMATION: Synthetic oligodeoxynucleotide (ODN)

<400> SEQUENCE: 15
gggtgggtgg gtagacgtta cc    22

<210> SEQ ID NO 16
<211> LENGTH: 16
<212> TYPE: DNA
<213> ORGANISM: Artificial sequence
<220> FEATURE:
<223> OTHER INFORMATION: Synthetic oligodeoxynucleotide (ODN)

<400> SEQUENCE: 16 gggggggtcaa gcttca    16

<210> SEQ ID NO 17
<211> LENGTH: 16
<212> TYPE: DNA
<213> ORGANISM: Artificial sequence
<220> FEATURE:
<223> OTHER INFORMATION: Synthetic oligodeoxynucleotide (ODN)

<400> SEQUENCE: 17
tcaagcttca gggggg    16

<210> SEQ ID NO 18
<211> LENGTH: 16
<212> TYPE: DNA
<213> ORGANISM: Artificial sequence
<220> FEATURE:
<223> OTHER INFORMATION: Synthetic oligodeoxynucleotide (ODN)

<400> SEQUENCE: 18

```
gggggggtcaa cgttca                                                      16

<210> SEQ ID NO 19
<211> LENGTH: 16
<212> TYPE: DNA
<213> ORGANISM: Artificial sequence
<220> FEATURE:
<223> OTHER INFORMATION: Synthetic   oligodeoxynucleotide (ODN)

<400> SEQUENCE: 19
cctcaagctt gagggg                                                       16

<210> SEQ ID NO 20
<211> LENGTH: 20
<212> TYPE: DNA
<213> ORGANISM: Artificial sequence
<220> FEATURE:
<223> OTHER INFORMATION: Synthetic   oligodeoxynucleotide (ODN)

<400> SEQUENCE: 20
gagcaagctg gaccttccat                                                   20

<210> SEQ ID NO 21
<211> LENGTH: 21
<212> TYPE: DNA
<213> ORGANISM: Artificial sequence
<220> FEATURE:
<223> OTHER INFORMATION: Synthetic   oligodeoxynucleotide (ODN)

<400> SEQUENCE: 21
gagcaagctg gtagacgtta g                                                 21

<210> SEQ ID NO 22
<211> LENGTH: 20
<212> TYPE: DNA
<213> ORGANISM: Artificial sequence
<220> FEATURE:
<223> OTHER INFORMATION: Synthetic   oligodeoxynucleotide (ODN)

<400> SEQUENCE: 22
gggcaagctg gacctggggg                                                   20

<210> SEQ ID NO 23
<211> LENGTH: 20
<212> TYPE: DNA
<213> ORGANISM: Artificial sequence
<220> FEATURE:
<223> OTHER INFORMATION: Synthetic   oligodeoxynucleotide (ODN)

<400> SEQUENCE: 23
ggggaagctg gacctggggg                                                   20

<210> SEQ ID NO 24
<211> LENGTH: 20
<212> TYPE: DNA
<213> ORGANISM: Artificial sequence
<220> FEATURE:
<223> OTHER INFORMATION: Synthetic   oligodeoxynucleotide (ODN)

<400> SEQUENCE: 24
gggcaagctg gaccttcggg                                                   20

<210> SEQ ID NO 25
<211> LENGTH: 22
<212> TYPE: DNA
<213> ORGANISM: Artificial sequence
```

```
<220> FEATURE:
<223> OTHER INFORMATION: Synthetic  oligodeoxynucleotide (ODN)

<400> SEQUENCE: 25
ggcaagctgg accttcgggg gg                                              22

<210> SEQ ID NO 26
<211> LENGTH: 20
<212> TYPE: DNA
<213> ORGANISM: Artificial sequence
<220> FEATURE:
<223> OTHER INFORMATION: Synthetic  oligodeoxynucleotide (ODN)

<400> SEQUENCE: 26
gagcaagctg gaccttccat                                                 20

<210> SEQ ID NO 27
<211> LENGTH: 21
<212> TYPE: DNA
<213> ORGANISM: Artificial sequence
<220> FEATURE:
<223> OTHER INFORMATION: Synthetic  oligodeoxynucleotide (ODN)

<400> SEQUENCE: 27
gagcaagctg gtagacgtta g                                               21

<210> SEQ ID NO 28
<211> LENGTH: 21
<212> TYPE: DNA
<213> ORGANISM: Artificial sequence
<220> FEATURE:
<223> OTHER INFORMATION: Synthetic  oligodeoxynucleotide (ODN)

<400> SEQUENCE: 28
gagcaagctg gtagacgtta g                                               21
```